(12) United States Patent
Sugita et al.

(10) Patent No.: US 9,090,819 B2
(45) Date of Patent: Jul. 28, 2015

(54) ORGANIC ELECTROLUMINESCENT ELEMENT, DISPLAY DEVICE, ILLUMINATING DEVICE AND CONDENSED POLYCYCLIC HETEROCYCLIC COMPOUND

(75) Inventors: Shuichi Sugita, Akishima (JP); Eisaku Katoh, Hachioji (JP); Motoaki Sugino, Akishima (JP); Rie Katakura, Hino (JP)

(73) Assignee: KONICA MINOLTA, INC. (JP)

( * ) Notice: Subject to any disclaimer, the term of this patent is extended or adjusted under 35 U.S.C. 154(b) by 442 days.

(21) Appl. No.: 13/378,120

(22) PCT Filed: Apr. 28, 2010

(86) PCT No.: PCT/JP2010/057560
§ 371 (c)(1),
(2), (4) Date: Dec. 14, 2011

(87) PCT Pub. No.: WO2010/150593
PCT Pub. Date: Dec. 29, 2010

(65) Prior Publication Data
US 2012/0085997 A1 Apr. 12, 2012

(30) Foreign Application Priority Data
Jun. 24, 2009 (JP) .................................. 2009-149731

(51) Int. Cl.
H01L 51/50 (2006.01)
C09K 11/06 (2006.01)
(Continued)

(52) U.S. Cl.
CPC .............. *C09K 11/06* (2013.01); *C07D 471/04* (2013.01); *C07D 471/14* (2013.01);
(Continued)

(58) Field of Classification Search
USPC .................. 428/690, 917; 313/504, 505, 506; 257/40, E51.05, E51.026, E51.032; 548/304.1, 418, 440; 564/26, 426, 434
See application file for complete search history.

(56) References Cited

U.S. PATENT DOCUMENTS 6,097,147 A 8/2000 Baldo et al.
2007/0224446 A1* 9/2007 Nakano et al. ................ 428/690
(Continued)

FOREIGN PATENT DOCUMENTS

EP 2123733 A2 11/2009
GB 2439030 A 12/2007
(Continued)

OTHER PUBLICATIONS

International Search Report for International Application No. PCT/JP2010/057560 mailed Aug. 17, 2010 with English translation.

*Primary Examiner* — Gregory Clark
(74) *Attorney, Agent, or Firm* — Cantor Colburn LLP

(57) ABSTRACT

Disclosed is an organic electroluminescent element which is characterized in that constituent layers including at least a phosphorescent light-emitting layer are provided between a pair of electrodes, and at least one of the constituent layers contains a compound represented by general formula (1). (In the formula, $A_1$, $A_2$ and $A_3$ each represents a substituent; n1 and n2 each represents an integer of 0-3; $X_1$ and $X_2$ each represents an oxygen atom, a sulfur atom, an alkylene group, an imino group, a carbonyl group, a sulfoxide group or a sulfonyl group, or alternatively $X_2$ represents a bonding hand; and $Z_1$, $Z_2$, $Z_3$ and $Z_4$ each represents an optionally substituted aromatic heterocyclic ring or an aromatic hydrocarbon ring, provided that all of the $Z_1$, $Z_2$, $Z_3$ and $Z_4$ are not aromatic hydrocarbon rings at the same time.)

Formula (1)

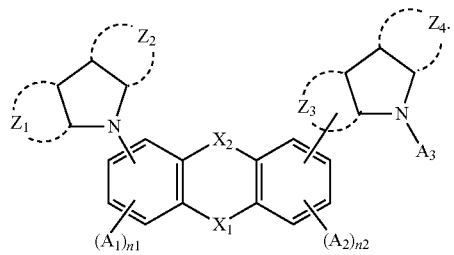

10 Claims, 3 Drawing Sheets

(51) Int. Cl.
*C07D 471/04* (2006.01)
*C07D 471/14* (2006.01)
*C07D 519/00* (2006.01)
*H01L 51/00* (2006.01)
*H05B 33/14* (2006.01)

(52) U.S. Cl.
CPC ......... *C07D 519/00* (2013.01); *H01L 51/0067* (2013.01); *H01L 51/0072* (2013.01); *H01L 51/0073* (2013.01); *H01L 51/0085* (2013.01); *H05B 33/14* (2013.01); *C09K 2211/1007* (2013.01); *C09K 2211/1011* (2013.01); *C09K 2211/1029* (2013.01); *C09K 2211/1033* (2013.01); *C09K 2211/1044* (2013.01); *C09K 2211/1059* (2013.01); *C09K 2211/1088* (2013.01); *C09K 2211/1092* (2013.01); *C09K 2211/1466* (2013.01); *C09K 2211/185* (2013.01); *H01L 51/0081* (2013.01); *H01L 51/0084* (2013.01); *H01L 51/0087* (2013.01); *H01L 51/0088* (2013.01); *H01L 51/5016* (2013.01); *H01L 2251/308* (2013.01)

(56) References Cited

U.S. PATENT DOCUMENTS

2009/0066226 A1    3/2009  Sugita et al.
2009/0284138 A1*  11/2009  Yasukawa et al. ............ 313/504

FOREIGN PATENT DOCUMENTS

| JP | 63-264692 A   | 11/1988 |
| JP | 3-255190 A    | 11/1991 |
| JP | 3093796 B2    | 10/2000 |
| JP | 2008-21687 A  | 1/2008  |
| JP | 2010-21336 A  | 1/2010  |
| JP | 2010-114180 A | 5/2010  |
| WO | 2006/095539 A1 | 9/2006 |
| WO | 2006/114966 A1 | 11/2006 |
| WO | 2007/054916 A2 | 5/2007 |
| WO | 2009/008100 A1 | 1/2009 |
| WO | 2010/004877 A1 | 1/2010 |

\* cited by examiner

LIGHT

ORGANIC ELECTROLUMINESCENT ELEMENT, DISPLAY DEVICE, ILLUMINATING DEVICE AND CONDENSED POLYCYCLIC HETEROCYCLIC COMPOUND

CROSS REFERENCE TO RELATED APPLICATIONS

This is a U.S. national stage of application No. PCT/JP2010/057560, filed on Apr. 28, 2010. Priority under 35 U.S.C. §119(a) and 35 U.S.C. §365(b) is claimed from Japanese Application No. 2009-149731, filed Jun. 24, 2009, the disclosure of which is also incorporated herein by reference.

TECHNICAL FIELD

The present invention relates to an organic electroluminescent element, a display device and a lighting device, and further related to a novel condensed polycyclic heterocyclic compound.

BACKGROUND

Conventionally, an emission type electronic display device includes an electroluminescence display (hereinafter, referred to as an ELD). A constituent element of ELD includes such as an inorganic electroluminescent element and an organic electroluminescent element (hereinafter, also referred to as an organic EL element).

An inorganic electroluminescent element has been utilized as a flat light source, however, requires a high voltage of alternating current to operate an emission element.

On the other hand, an organic electroluminescent element is an element provided with a constitution comprising an emission layer containing a emitting substance being sandwiched with a cathode and an anode, and an exciton is generated by an electron and a positive hole being injected into the emission layer to be recombined, resulting emission utilizing light release (fluorescence and phosphorescence) at the time of deactivation of said exciton; the emission is possible at a voltage of approximately a few to a few tens volts, and an organic electroluminescent element is attracting attention with respect to such as superior viewing angle and high visual recognition due to a self-emission type as well as space saving and portability due to a completely solid element of a thin layer type.

In an organic electroluminescence in view of the future practical application, desired has been development of an organic EL element which efficiently emits at a high luminance with a low electric consumption. Examples of such technologies are a slight amount of a fluorescent substance doped in a stilbene derivative, distyrylarylene derivative or a tristyrylarylene derivative, to achieve improved emission luminance and a prolonged lifetime of an element (for example, refer to Patent Document 1). Further, there are known such as an element having an organic emission layer comprising a 8-hydroxyquinoline aluminum complex as a host compound which is doped with a slight amount of a fluorescent substance (for example, refer to Patent Document 2), and an element having an organic emission layer comprising a 8-hydroxyquinoline aluminum complex as a host compound which is doped with quinacridone type dye (for example, refer to Patent Document 3).

Regarding to the technologies disclosed in the above-described Patent Documents, when emission from an excited singlet is utilized, since a generation ratio of a singlet exciton to a triplet exciton is 1/3, that is, a generation probability of an emitting exciton species is 25% and a light taking out efficiency is approximately 20%, the limit of a quantum efficiency (next) of taking out is said to be 5%.

However, since an organic EL element which utilizes phosphorescence from an excited triplet has been reported from Princeton University (for example, refer to Non-Patent Document 1), researches on materials exhibiting phosphorescence at room temperature have come to be active (for example, refer to Non-Patent Document 2 and Patent Document 4).

Since the upper limit of internal quantum efficiency becomes 100% by utilization of an excited triplet, which is principally 4 times of the case of an excited singlet, it may be possible to achieve almost the same ability as a cooled cathode ray tube to attract attention also for an illumination application. For example, many compounds mainly belonging to heavy metal complexes such as iridium complexes have been synthesized and studied (for example, refer to Non-Patent Document 3).

Further, utilization of tris(2-phenylpyridine)iridium as a dopant has been studied (for example, refer to Non-Patent Document 2). In addition to these, there have been studied to use $L_2Ir(acac)$ such as $(ppy)_2Ir(acac)$ as a dopant (for example, refer to Non-Patent Document 4). Also there have been studied to use compounds as a dopant, such as tris(2-(p-tolyl)pyridine)iridium $(Ir(ptpy)_3)$, tris(benzo[h]quinoline)iridium $(Ir(bzq)_3)$ and $Ir(bzq)_2$ $CIP(Bu)_3$ (for example, refer to Non Patent Document 5).

Further, to obtain high emission efficiency, a hole transporting compound is known to use as a host of a phosphorescent compound (for example, refer to Non-Patent Document 6).

Further, various types of electron transporting materials have been used as a host of a phosphorescent compound doped with a new iridium complex for example, refer to Non-Patent Document 4). In addition, a high emission efficiency has been achieved by introduction of a hole block layer (for example, refer to Non-Patent Document 5).

Moreover, there is disclosed materials of an electron transport property having a chemical constitution in which a nitrogen-containing aromatic ring compound extends in two directions or in three directions form a center of a 3 ring type condensed heterocyclic compound (for example, refer to Patent Documents 5, 6 and 7).

Presently, although it is investigated to make further higher efficiency and longer lifetime of the light emission of the organic EL element using this phosphorescence luminescence, and the external extraction efficiency of about 20% which is a theoretical limit was attained about green luminescence, it is only at a low current portion (low luminance area), and the theoretical limit has not been yet attained in a high current region (high luminance region). Furthermore, sufficient efficiency about other luminescent colors has not been obtained, and further improvement is required. A development of the organic EL device which emits light to high-intensity efficiently with low power is desired in the organic EL element towards a future practical application. Especially, regarding to the organic EL element of blue phosphorescence luminescence, it is required that it emits light efficiently with a long lifetime.

PRIOR ART DOCUMENTS

Patent Documents

Patent Document 1: Japanese Registered Patent No. 3093796
Patent Document 2: Japanese Patent Application Publication (hereinafter referred to as JP-A) No. 63-264692

Patent Document 3: JP-A No. 3-255190
Patent Document 4: U.S. Pat. No. 6,097,147
Patent Document 5: WO 06/95539
Patent Document 6: WO 09/8100
Patent Document 7: WO 07/54916

Non-Patent Documents

Non-Patent Document 1: M. A. Baldo et al., Nature, Vol. 395, pages 151-154 (1998)
Non-Patent Document 2: M. A. Baldo et al., Nature, Vol. 403, No. 17, pages 750-753 (2000)
Non-Patent Document 3: S. Lamansky et al., J. Am. Chem. Soc., Vol. 123, page 4304 (2001)
Non-Patent Document 4: M. E. Tompson et al., The 10th International Workshop on Inorganic and Organic Electroluminescence (EL '00, Hamamatsu)
Non-Patent Document 5: Moon-Jae Youn. Og, Tetsuo Tsutsui et al., The 10th International Workshop on Inorganic and Organic Electroluminescence (EL '00, Hamamatsu)
Non-Patent Document 6: Ikai et al., The 10th International Workshop on Inorganic and Organic Electroluminescence (EL '00, Hamamatsu)

DISCLOSURE OF THE INVENTION

Problems to be Solved by the Invention

An object of the present invention is to provide an organic EL element exhibiting high light emitting efficiency, high external quantum efficiency with long lifetime, and also to provide a lighting device and a display device provided with the aforesaid organic electroluminescence element, and further, to provide a novel condensed polycyclic heterocyclic compound.

Means to Solve the Problems

An object of the present invention described above has been achieved by the following constitutions.
1. An organic electroluminescence element comprising a pair of electrodes and constituting layers which includes a phosphorescence emitting layer sandwiched between the pair of electrodes,
wherein at least one of the constituting layers contains a compound represented by Formula (1).

Formula (1)

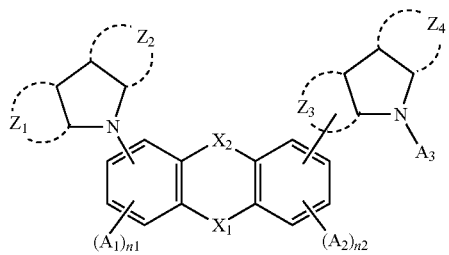

(In Formula, $A_1$, $A_2$ and $A_3$ each represent a substituent. n1 and n2 each represent an integer of 0 to 3. $X_1$ and $X_2$ each represent an oxygen atom, a sulfur atom, an alkylene group, an imino group, a carbonyl group, a sulfoxide group, or a sulfonyl group, or $X_2$ may be a single bond. $Z_1$, $Z_2$, $Z_3$ and $Z_4$ each represent an aromatic heterocycle or an aromatic hydrocarbon ring, both of which may have a substituent, provided that all of $Z_1$, $Z_2$, $Z_3$ and $Z_4$ do not represent an aromatic hydrocarbon ring at the same time.)

2. The organic electroluminescence element described in the aforesaid item 1, wherein the compound represented by Formula (1) is further represented by Formula (2).

Formula (2)

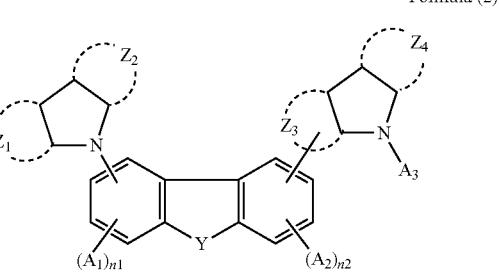

(In Formula, $A_1$, $A_2$ and $A_3$ each represent a substituent n1 and n2 each represent an integer of 0 to 3. $Z_1$, $Z_2$, $Z_3$ and $Z_4$ each represent an aromatic heterocycle or an aromatic hydrocarbon ring, both of which may have a substituent, provided that all of $Z_1$, $Z_2$, $Z_3$ and $Z_4$ do not represent an aromatic hydrocarbon ring at the same time. Y represents an oxygen atom, a sulfur atom, an imino group, a sulfoxide group, or a sulfonyl group.)

3. The organic electroluminescence element described in the aforesaid item 2, wherein the compound represented by Formula (2) is further represented by Formula (3).

Formula (3)

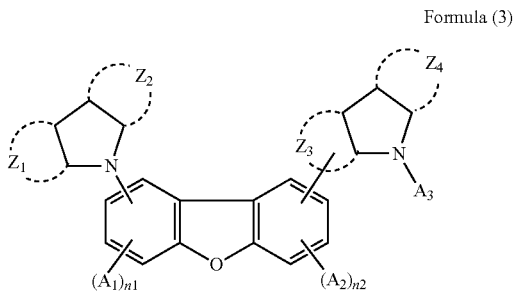

(In Formula, $A_1$, $A_2$ and $A_3$ each represent a substituent. n1 and n2 each represent an integer of 0 to 3. $Z_1$, $Z_2$, $Z_3$ and $Z_4$ each represent an aromatic heterocycle or an aromatic hydrocarbon ring, both of which may have a substituent, provided that all of $Z_1$, $Z_2$, $Z_3$ and $Z_4$ do not represent an aromatic hydrocarbon ring at the same time.)

4. The organic electroluminescence element described in the aforesaid item 3, wherein the compound represented by Formula (3) is further represented by Formula (4).

Formula (4)

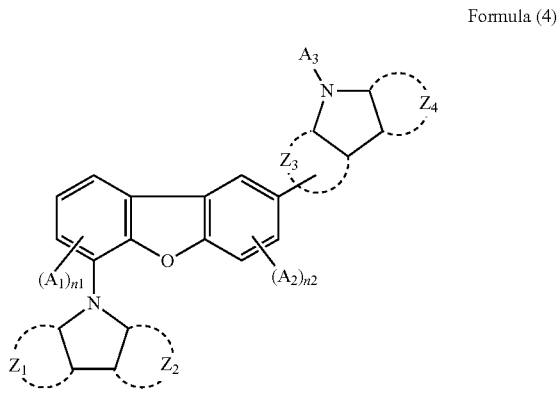

(In Formula, $A_1$, $A_2$ and $A_3$ each represent a substituent n1 and n2 each represent an integer of 0 to 3. $Z_1$, $Z_2$, $Z_3$ and $Z_4$ each represent an aromatic heterocycle or an aromatic hydrocarbon ring, both of which may have a substituent, provided that all of $Z_1$, $Z_2$, $Z_3$ and $Z_4$ do not represent an aromatic hydrocarbon ring at the same time.)

5. The organic electroluminescence element described in any one of the aforesaid items 1 to 4, wherein $Z_2$ and $Z_4$ in Formulas (1), (2), (3) and (4) each represent an aromatic heterocycle.
6. The organic electroluminescence element described in any one of the aforesaid items 1 to 5, wherein the phosphorescence emitting layer contains the compound represented by any one of Formulas (1), (2), (3) and (4).
7. The organic electroluminescence element described in any one of the aforesaid items 1 to 6, wherein the at least one of the constituting layers is a hole blocking layer and the hole blocking layer contains the compound represented by any one of Formulas (1), (2), (3) and (4).
8. The organic electroluminescence element described in any one of the aforesaid items 1 to 7, emitting a blue light.
9. The organic electroluminescence element described in any one of the aforesaid items 1 to 7, emitting a white light.
10. A display device comprising the organic electroluminescence element of the aforesaid item 9.
11. A lighting device comprising the organic electroluminescence element of the aforesaid item 9
12. A display device comprising the lighting device of the aforesaid item 11 and a liquid crystal element as a display means.
13. A condensed polycyclic heterocyclic compound represented by Formula (3).

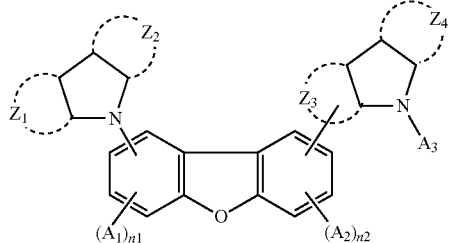

Formula (3)

(In Formula, $A_1$, $A_2$ and $A_3$ each represent a substituent. n1 and n2 each represent an integer of 0 to 3. $Z_1$, $Z_2$, $Z_3$ and $Z_4$ each represent an aromatic heterocycle or an aromatic hydrocarbon ring, both of which may have a substituent, provided that all of $Z_1$, $Z_2$, $Z_3$ and $Z_4$ do not represent an aromatic hydrocarbon ring at the same time.)

Effects of the Invention

By the present invention, it has been achieved to provide an organic electroluminescent element which exhibits high light emitting efficiency, high external quantum efficiency with long lifetime, and also to provide a lighting device and a display device provided with the aforesaid organic electroluminescence element. Further, it has been achieved to provide a novel condensed polycyclic heterocyclic compound.

EMBODIMENTS TO CARRY OUT THE INVENTION

Figure 1:
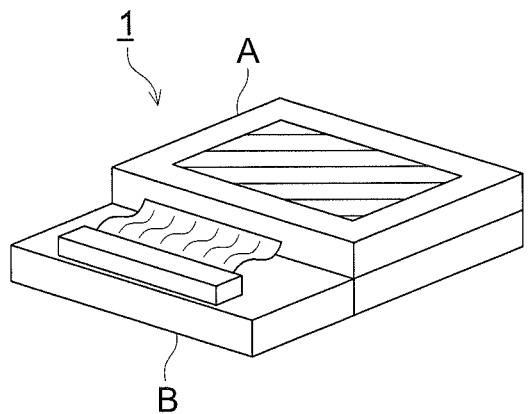
FIG. 1 is a schematic drawing to show an example of a display device constituted of an organic EL element.

The present invention will be detailed below.
The present invention is characterized in as follows. In an organic electroluminescence element comprising a pair of electrodes and constituting layers including a phosphorescence emitting layer sandwiched between the a pair of electrodes, at least one of the constituting layers contains a compound represented by any one of Formulas (1), (2), (3) and (4). The composing layer containing the compound represented by any one of the aforesaid Formulas (1), (2), (3) and (4) is preferably the phosphorescence emitting layer or a hole blocking layer. Especially, a hole blocking layer is preferable.
Hereafter, the details of each structural element of the organic EL element of the present invention will be described successively.
The compounds relating to the present invention will be described.

<Compounds Represented by Formulas (1) to (4)>

The compounds represented by Formulas (1) to (4) relating to the present invention will be described.
Examples of a substituent represented by $A_1$, $A_2$ and $A_3$ in Formulas (1) to (4) include: an alkyl group (preferably having 1 to 20 carbon atoms, and more preferably having 1 to 12 carbon atoms, and still more preferably having 1 to 8 carbon atoms, for example, a methyl, ethyl, iso-propyl, t-butyl n-octyl, n-decyl, n-hexadecyl, cyclopropyl, cyclopentyl and cyclohexyl group); an alkenyl group (preferably having 2 to 20 carbon atoms, and more preferably having 2 to 12 carbon atoms, and still more preferably having 2 to 8 carbon atoms, for example, a vinyl, allyl, 2-butenyl and 3-pentenyl group); an alkynyl group (preferably having 2 to 20 carbon atoms, and more preferably having 2 to 12 carbon atoms, and still more preferably having 2 to 8 carbon atoms, for example, a propargyl and 3-pentynyl group); an aryl group (preferably having 6 to 30 carbon atoms, and more preferably having 6 to 20 carbon atoms, and still more preferably having 6 to 12 carbon atoms, for example, a phenyl, p-methylphenyl, naphthyl and pyridyl phenyl group); an amino group (preferably having 0 to 20 carbon atoms, and more preferably having 0 to 10 carbon atoms, and still more preferably having 0 to 6 carbon atoms, for example, an amino, methylamino, dimethylamino, diethylamino and dibenzylamino group); an alkoxy group (preferably having 1 to 20 carbon atoms, and more preferably having 1 to 12 carbon atoms, and still more preferably having 1 to 8 carbon atoms, for example, a methoxy, ethoxy and butoxy group); an aryloxy group (preferably having 6 to 20 carbon atoms, and more preferably having 6 to 16 carbon atoms, and still more preferably having 6 to 12 carbon atoms, for example, a phenoxy and 2-naphthyloxy group); an acyl group (preferably having 1 to 20 carbon atoms, and more preferably having 1 to 16 carbon atoms, and still more preferably having 1 to 12 carbon atoms, for example, an acetyl, benzoyl, formyl and pivaloyl group); an alkoxycarbonyl group (preferably having 2 to 20 carbon atoms, and more preferably having 2 to 16 carbon atoms, and still more preferably having 2 to 12 carbon atoms, for example, a methoxycarbonyl and ethoxycarbonyl group); an aryloxycarbonyl group (preferably having 7 to 20 carbon atoms, and more preferably having 7 to 16 carbon atoms, and still more preferably having 7 to 10 carbon atoms, for example, a phenoxycarbonyl group); an acyloxy group (preferably having 2 to 20 carbon atoms, and more preferably having 2 to 16 carbon atoms, and still more preferably having 2 to 10 carbon atoms, for example, an acetoxy and benzoyloxy group); an acylamino group (preferably having 2 to 20 carbon atoms, and more preferably having 2 to 16 carbon atoms, and still more preferably having 2 to 10 carbon atoms, for example, an acetylamino and benzoylamino group); an alkoxycarbonylamino group (preferably having 2 to 20 carbon atoms, and more preferably having 2 to 16 carbon atoms, and still more preferably having 2 to 12 carbon atoms, for example, a methoxycarbonylamino group); an aryloxycarbonylamino group (preferably having 7 to 20 carbon atoms, and more preferably having 7 to 16 carbon atoms, and still more preferably having 7 to 12 carbon atoms, for example, a phenoxycarbonylamino group); a sulfonylamino group (preferably having 1 to 20 carbon atoms, and more preferably having 1 to 16 carbon atoms, and still more preferably having 1 to 12 carbon atoms, for example, a methanesulfonylamino and benzenesulfonylamino group); a sulfamoyl group (preferably having 0 to 20 carbon atoms, and more preferably having 0 to 16 carbon atoms, and still more preferably having 0 to 12 carbon atoms, for example, a sulfamoyl, methylsulfamoyl, dimethylsulfamoyl and phenylsulfamoyl group); a carbamoyl group (preferably having 1 to 20 carbon atoms, and more preferably having 1 to 16 carbon atoms, and still more preferably having 1 to 12 carbon atoms, for example, a carbamoyl, methylcarbamoyl, diethylcarbamoyl and phenylcarbamoyl group); an alkylthio group (preferably having 1 to 20 carbon atoms, and more preferably having 1 to 16 carbon atoms, and still more preferably having 1 to 12 carbon atoms, for example, a methylthio and ethylthio group); an arylthio group (preferably having 6 to 20 carbon atoms, and more preferably having 6 to 16 carbon atoms, and still more preferably having 6 to 12 carbon atoms, for example, a phenylthio group); a sulfonyl group (preferably having 1 to 20 carbon atoms, and more preferably having 1 to 16 carbon atoms, and still more preferably having 1 to 12 carbon atoms, for example, a mesyl and tosyl group); a sulfinyl group (preferably having 1 to 20 carbon atoms, and more preferably having 1 to 16 carbon atoms, and still more preferably having 1 to 12 carbon atoms, for example, a methanesulfinyl and benzenesulfinyl group); a ureido group (preferably having 1 to 20 carbon atoms, and more preferably having 1 to 16 carbon atoms, and still more preferably having 1 to 12 carbon atoms, for example, a ureido, methylureido and phenylureido group); a phosphoramide group (preferably having 1 to 20 carbon atoms, and more preferably having 1 to 16 carbon atoms, and still more preferably having 1 to 12 carbon atoms, for example, a diethyl phosphoramide and phenyl phosphoramide group); a hydroxyl group, a mercapto group, a halogen atom (for example, a fluorine atom, a chlorine atom, a bromine atom and an iodine atom), a cyano group, a sulfo group, a carboxyl group, a nitro group, a hydroxamic acid group, a sulfino group, a hydrazino group, an imino group, a heterocyclic group (containing in the molecule, for example, a nitrogen atom, an oxygen atom, a sulfur atom and a selenium atom as a hetero atom, and preferably having 1 to 30 carbon atoms, and more preferably having 1 to 20 carbon atoms. Examples thereof are: an imidazolyl, pyridyl, a furyl, piperidyl and morpholino group). These substituents may be further substituted with a substituent. Further, a plurality of these substituents may combine with each other to form a ring if possible.

In Formula (1), preferable groups represented by $X_1$ and $X_2$ are an oxygen atom, a sulfur atom, or an imino group, and more preferable group is an oxygen atom. Preferably, $X_2$ is a single bond. In Formula (2), preferable groups represented by Y are an oxygen atom, a sulfur atom, or an imino group, and more preferable group is an oxygen atom.

In Formulas (1) to (4), $Z_1$, $Z_2$, $Z_3$ and $Z_4$ each represent a group of atoms which forms an aromatic heterocycle or an aromatic hydrocarbon ring. It is preferable that $Z_2$ and $Z_4$ each represent an aromatic heterocycle.

Examples of an aromatic heterocycle include: a furan ring, a thiophene ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a thiazole ring, an indole ring, a benzimidazole ring, a benzothiazole ring, a benzoxazole ring, a quinoxaline ring, a quinazoline ring, a phthalazine ring, a carbazole ring, a carboline ring, a diazacarbazole ring (indicating a ring structure in which one of the carbon atoms constituting the carboline ring in the aforesaid carbolinyl group is replaced with a nitrogen atom). Examples of an aromatic hydrocarbon ring include: a benzene ring, a biphenyl ring, a naphthalene ring, an azulene ring, an anthracene ring, a phenanthrene ring, a pyrene ring, a chrysene ring, a naphthacene ring, a triphenylene ring, o-terphenyl ring, m-terphenyl ring, a p-terphenyl ring, an acenaphthene ring, a coronene ring, a fluorene ring, a fluoanthrene ring, a naphthacene ring, a pentacene ring, a perylene ring, a pentaphene ring, a picene ring, a pyrene ring, a pyranthrene ring, and an anthraanthrene ring. Further, these aromatic hydrocarbon rings and aromatic heterocycles may have a substituent. As substituents, the same substituents indicated above are cited. Among substituents, preferable are a pyridyl group and a phenyl group.

Specific examples of a compound represented by the aforesaid Formulas (1) to (4) of the present invention are shown below. However, the present invention is not limited to these.

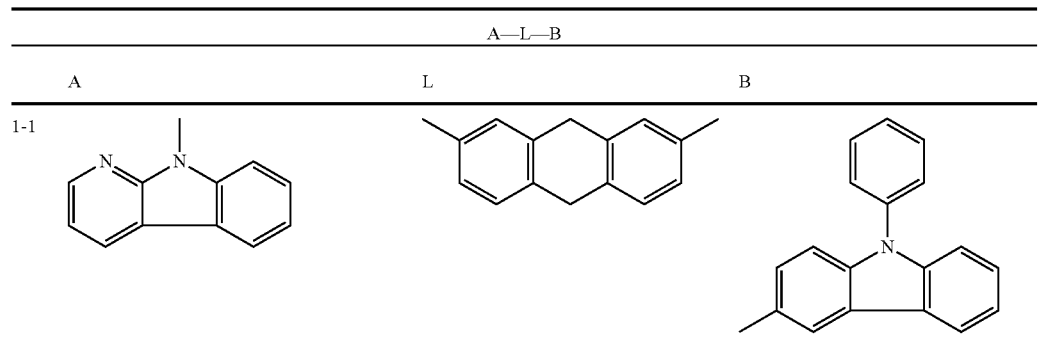

-continued
| A | L | B |
|---|---|---|
1-2 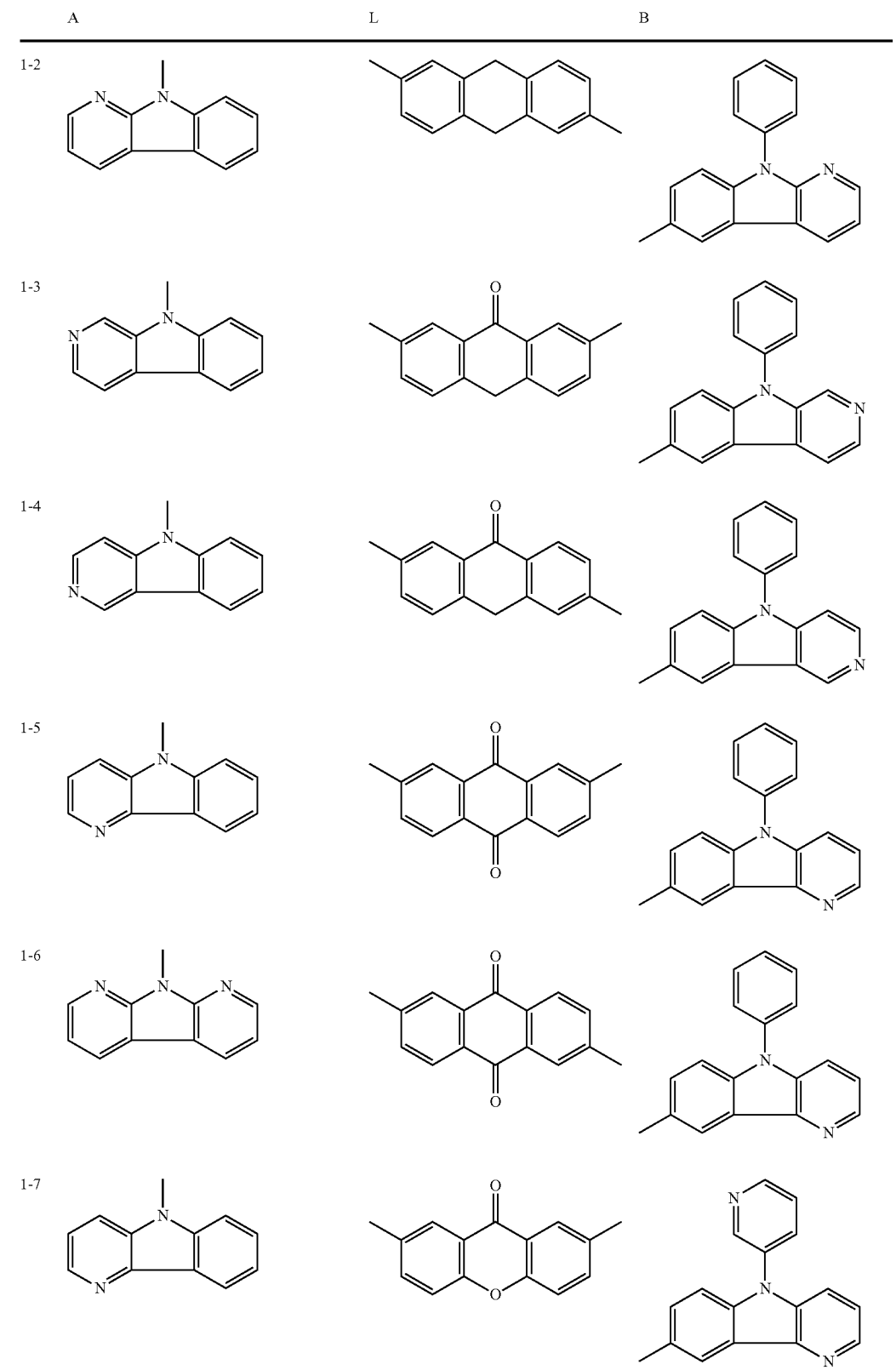
1-3
1-4
1-5
1-6
1-7

-continued
| | A | L | B |
|---|---|---|---|
| 1-8 | 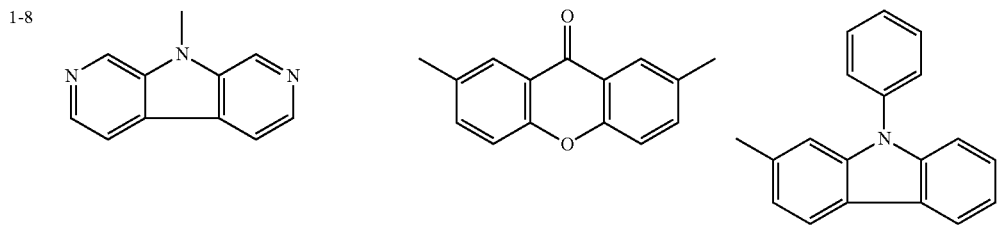 | | |
| 1-9 | 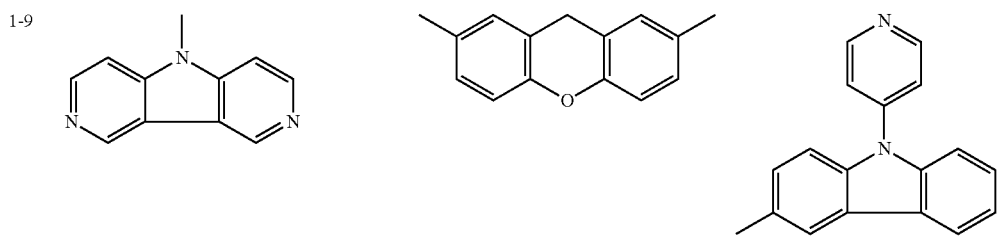 | | |
| 1-10 | 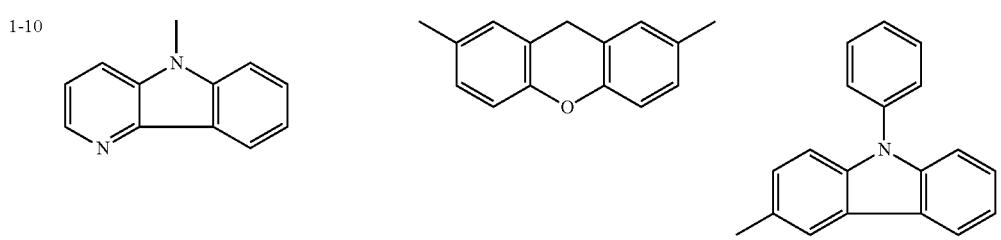 | | |
| 1-11 | 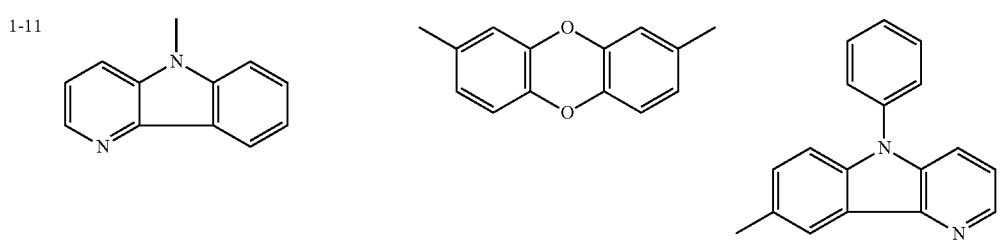 | | |
| 1-12 | 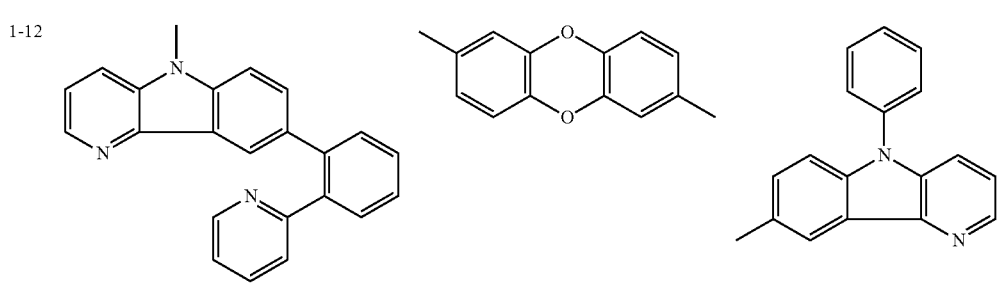 | | |
| 1-13 | 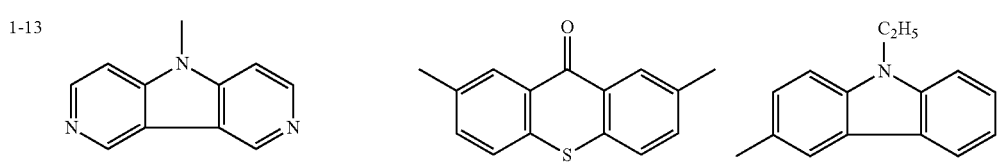 | | |

-continued
| | A—L—B | |
|---|---|---|
| A | L | B |
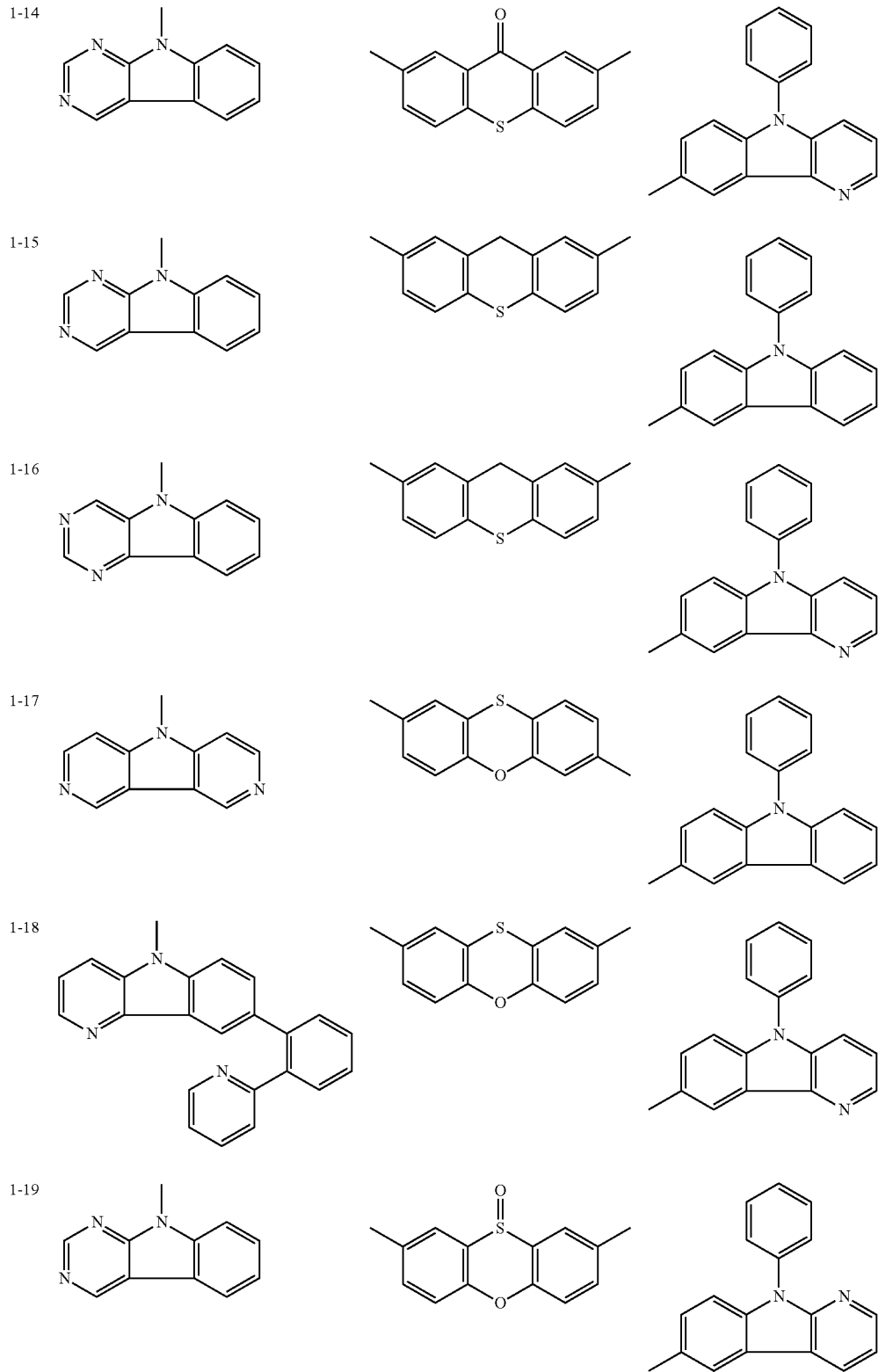

-continued
| | A | L | B |
|---|---|---|---|
| 1-20 | 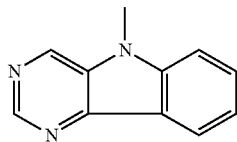 | 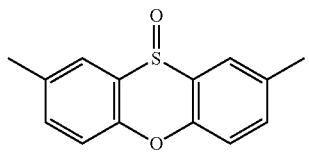 | 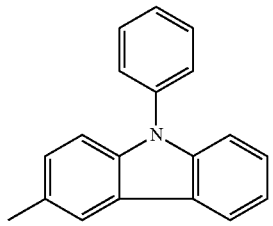 |
| 1-21 | 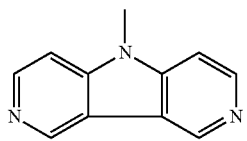 | 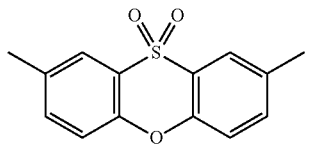 | 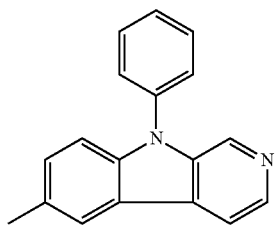 |
| 1-22 | 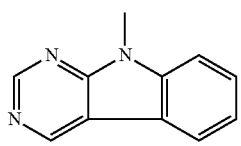 | 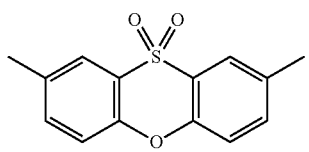 | 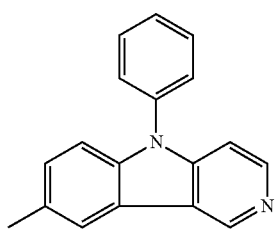 |
| 1-23 | 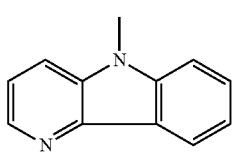 | 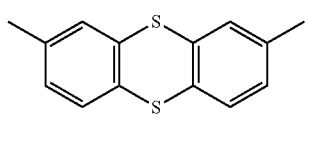 | 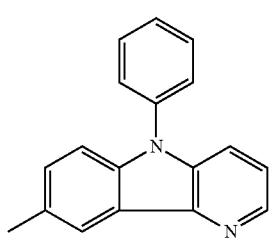 |
| 1-24 | 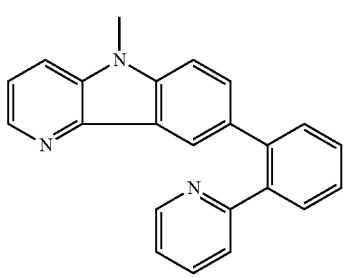 | 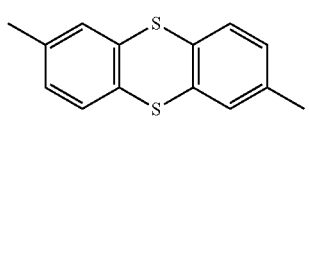 | 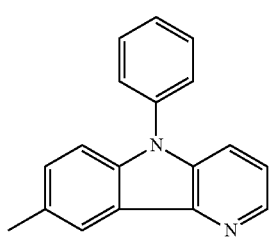 |
| 1-25 | 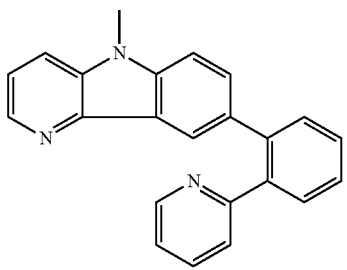 | 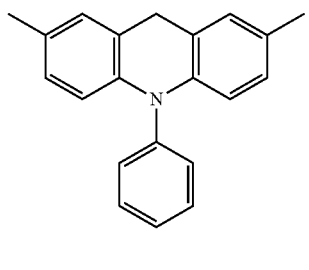 | 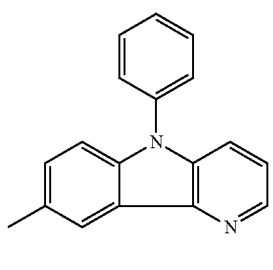 |

-continued
| | A | L | B |
|---|---|---|---|
| 1-26 | 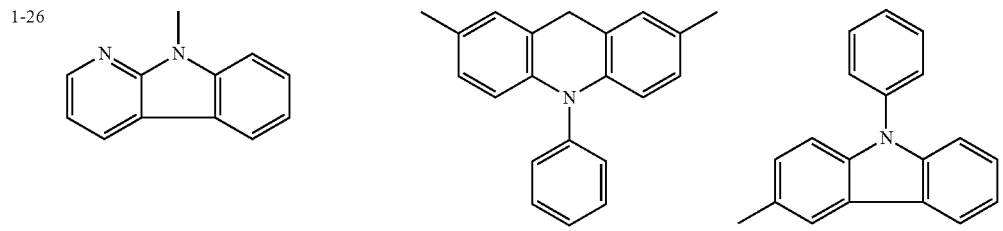 | | |
| 1-27 | 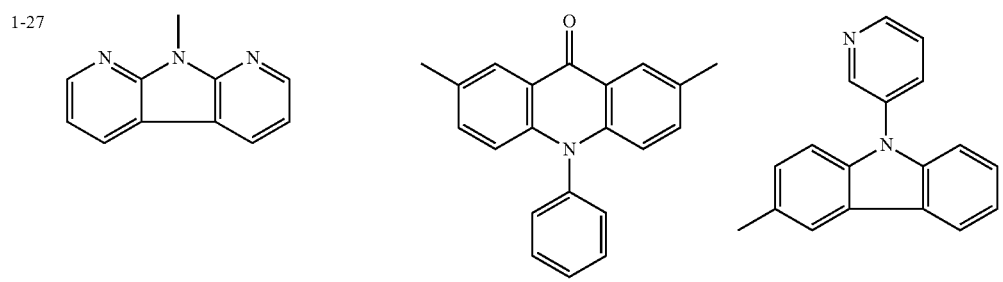 | | |
| 1-28 | 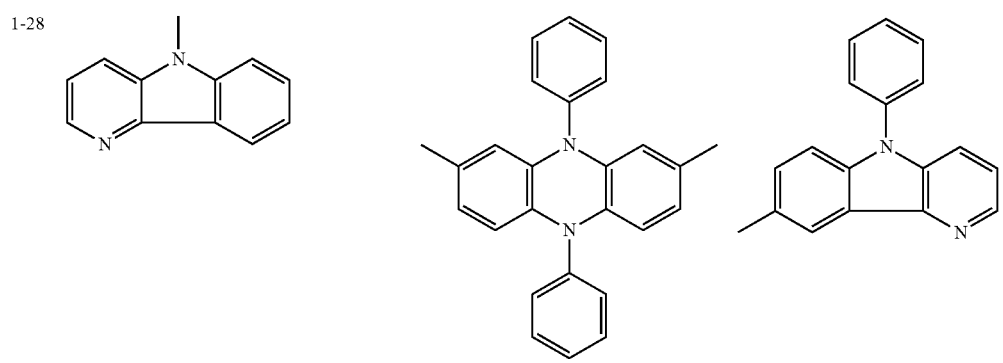 | | |
| 1-29 | 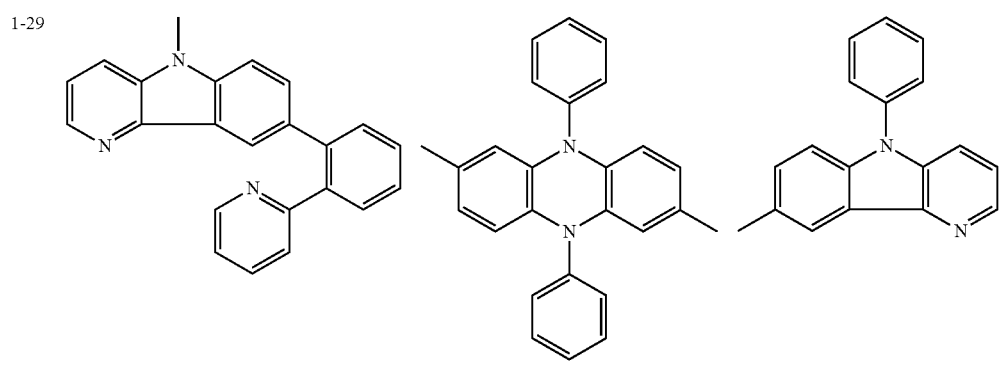 | | |
| 2-1 | 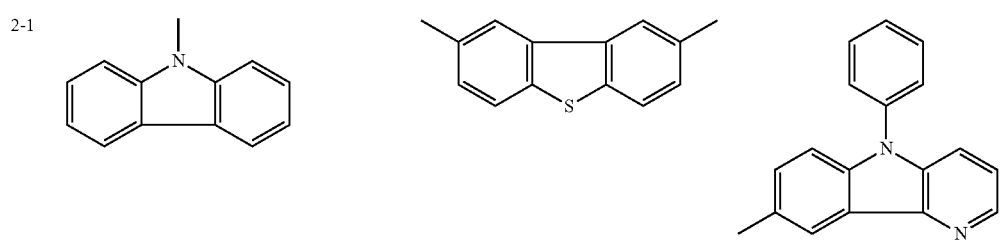 | | |

-continued

| | A | L | B |
|---|---|---|---|
| 2-2 | | | |
| 2-3 | | | |
| 2-4 | | | |
| 2-5 | | | |
| 2-6 | | | |
| 2-7 | | | |

-continued
| | A | L | B |
|---|---|---|---|
| 2-8 | | | |
| 2-9 | | | |
| 2-10 | | | |
| 2-11 | | | |
| 2-12 | | | |
| 3-1 | | | |
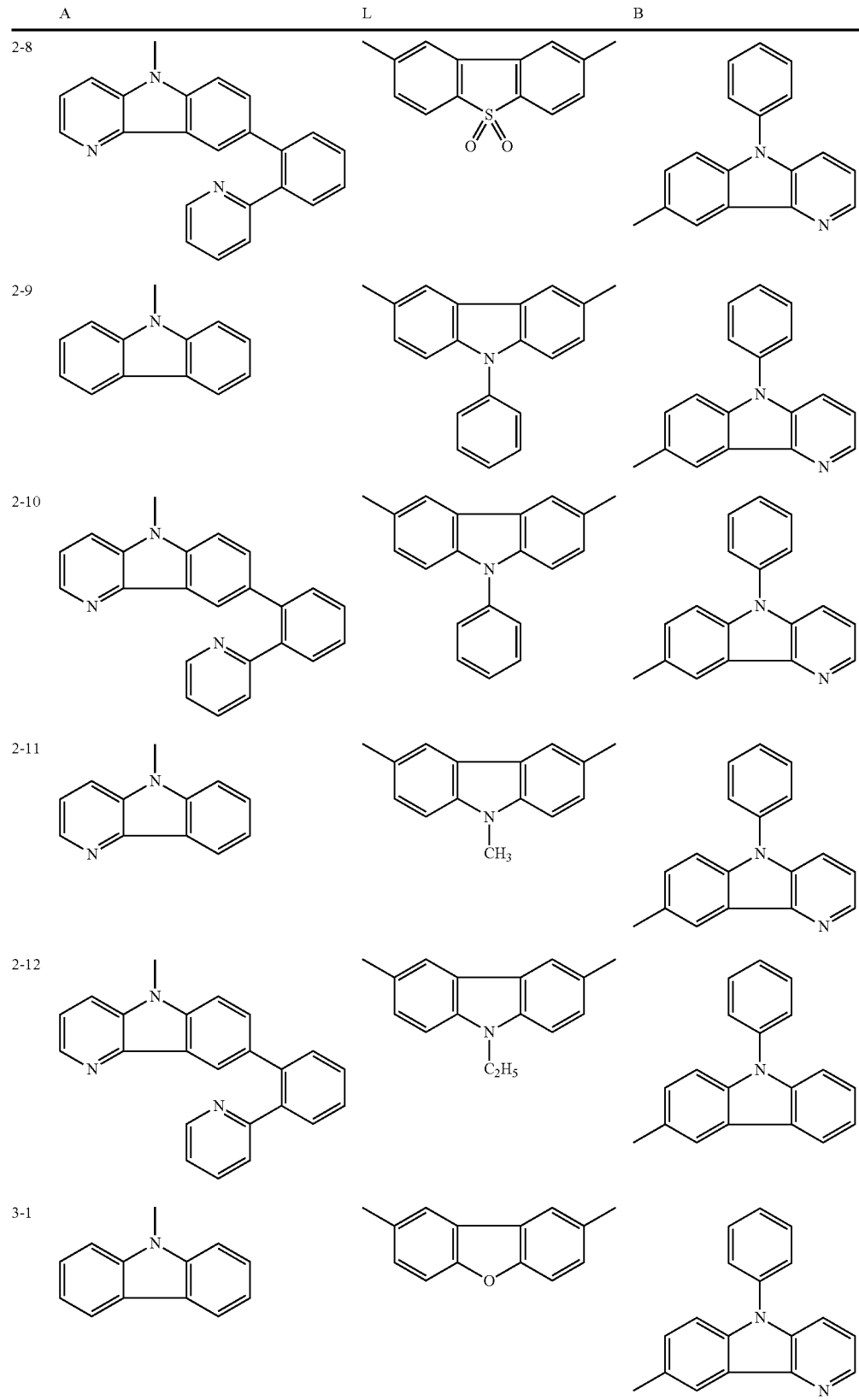

-continued
| | A | L | B |
|---|---|---|---|
| 3-2 | | | |
| 3-3 | | | |
| 3-4 | | | |
| 3-5 | | | |
| 3-6 | | | |
| 3-7 | | | |
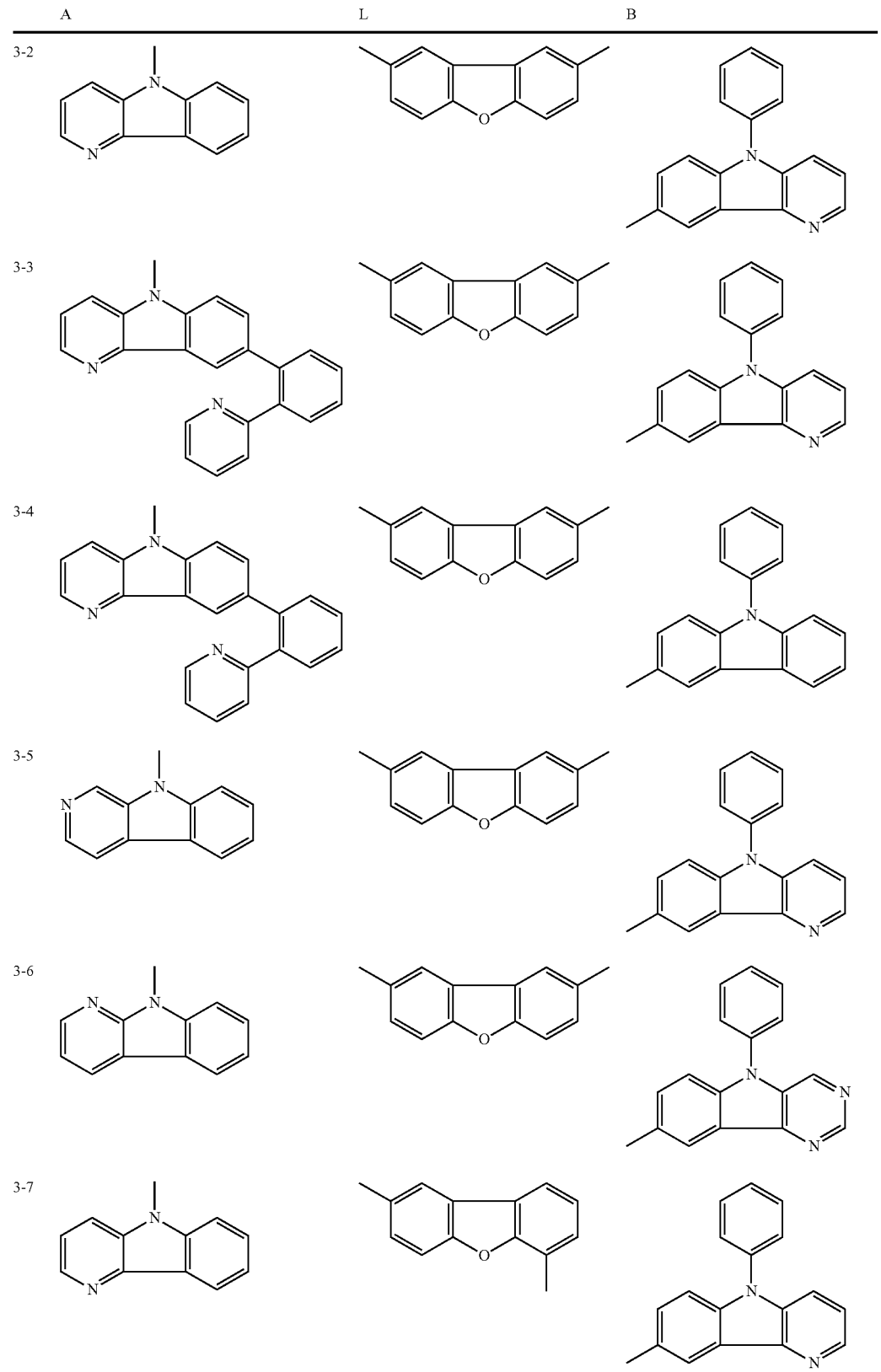

-continued
| | A | L | B |
|---|---|---|---|
| 3-8 | 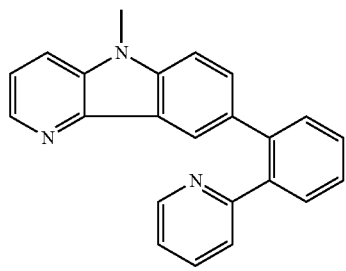 | 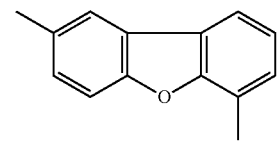 | 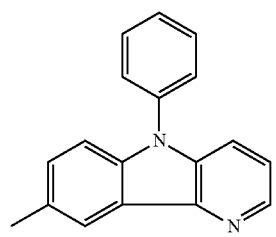 |
| 3-9 | 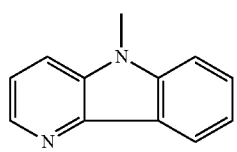 | 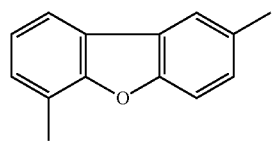 | 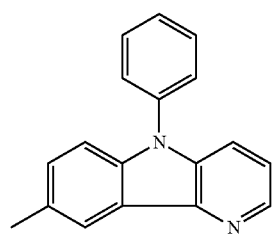 |
| 3-10 | 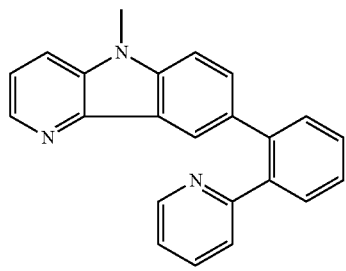 | 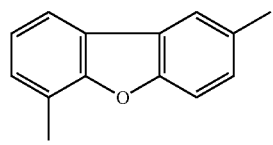 | 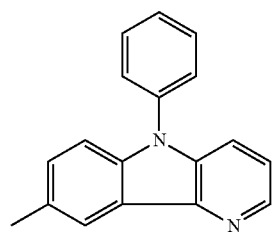 |
| 3-11 | 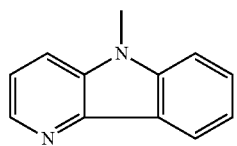 | 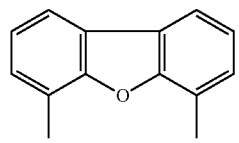 | 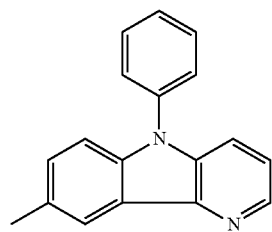 |
| 3-12 | 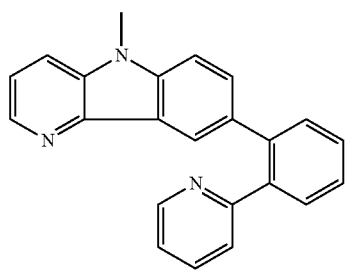 | 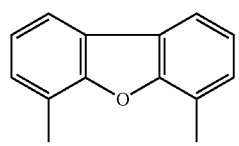 | 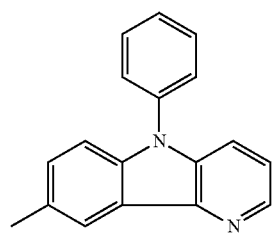 |

A synthetic example of the representative compound according to the present invention will be described below. However, the present invention will not be limited to these.

Synthetic Example

Synthesis of Example Compound 3-3

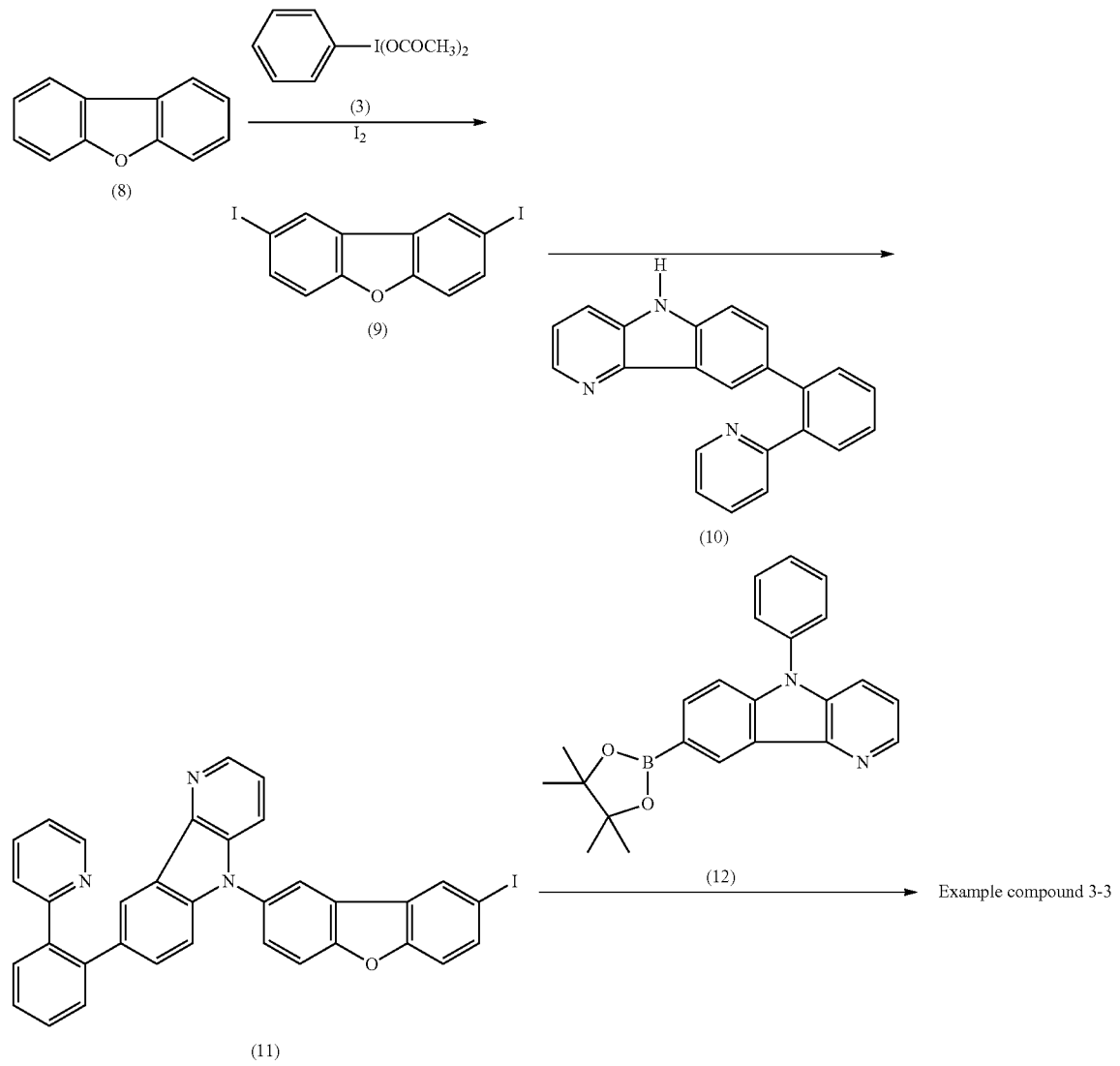

To a solution of 22 ml of acetic acid and 22 ml of acetic anhydride were added 6.3 g of Compound (3) and 4.7 g of iodine. Further, 3 g of Compound (8) was added thereto during 5 minutes, and was added a few drops of sulfuric acid, followed by stirring for 20 minutes. The reaction solution was poured into 300 ml of 5% sodium sulfite aqueous solution. After adding 1 g of sodium carbonate, raw crystals were obtained by filtration under a reduced pressure. The obtained raw crystals were recrystallized from chloroform to produce 4.7 g of Compound (9) (yield: 62.2%).

There were added 4.7 g of Compound (9), 3.2 g of Compound (10), 2.3 g of potassium carbonate, 2.1 g of Cu powders and 60 ml of dry DMAc, and the mixture was stirred under a nitrogen gas stream for 20 hours. The inner temperature was kept at 135 to 137° C. The insoluble materials were filtered under a reduced pressure. To the filtrate was added 15 ml of water to result in precipitation of a solid. The solid was filtered under a reduced pressure. The obtained raw product was purified using a column chromatography (silica gel, developer: mixture of ethyl acetate and toluene) to produce 3.4 g of Compound (11) (yield: 50%).

After mixing 3.4 g of Compound (11), 2.3 g of Compound (12), 1.0 g of potassium carbonate fine powders and 50 ml of DMSO, the inside of the reactor was replaced with a nitrogen gas stream for 20 minutes. Subsequently, 0.45 g of PdCl$_2$dppf was added to the reaction mixture and it was stirred while heating for 2 hours. The inner temperature was kept at 75 to 80° C. Then the reaction mixture was cooled to mom temperature followed by adding 4 ml of water. It was stirred at mom temperature and the precipitated crystals were filtered under a reduced pressure. The obtained raw product was purified using a column chromatography (silica gel, developer: mixture of ethyl acetate and toluene). Then it was recrystallized from a mixture of THF and MeOH to produce 2.7 g of Example compound 3-3 (yield: 66.0%). The chemical structure was determined with ¹H-NMR spectrum and mass spectrum.

¹H-NMR data (400 MHz, CDCl₃): δ=8.75 (d, 1H), 8.7-8.6 (m, 3H), 8.50 (d, 1H), 8.34 (d, 1H), 8.15 (d, 1H), 8.0-7.5 (m, 15H), and 7.5-7.0 (m, 9H).

Synthetic Example

Synthesis of Example Compound 3-10

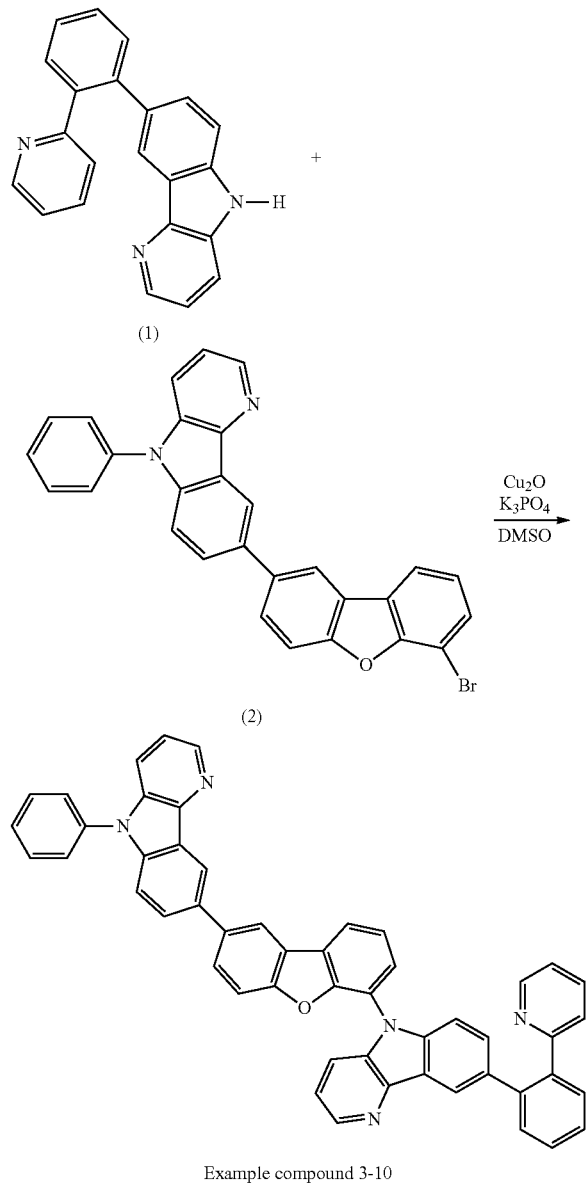

Example compound 3-10

Under a nitrogen gas stream, there were placed 3.3 g (0.0102 mol) of Compound (1), 5.0 g (×1.0 mol) of Compound (2), 3.9 g (×1.8 mol) of potassium phosphate, 50 ml of DMSO, 0.29 g (×0.20 mol) of Cu₂O and 0.76 g (×0.40 mol) of dipyvaloylmethane. Then the mixture was stored at 150 to 160° C. for 8 hours. Subsequently, there were added a saturated aqueous sodium chloride solution and THF. After removing the insoluble matter, the organic phase was concentrated under a reduced pressure. Then the concentrated product was purified using a column chromatography (silica gel, developer: mixture of toluene and THF). The obtained pale brown past was recrystallized from acetonitrile to obtain 5.2 g of Example compound 3-10 (yield: 70%).

The compounds represented by Formulas (1), (2), (3) and (4) relating to the present invention are applied to the materials for an organic EL element (for example, a backlight, a flat panel display, an illumination light source, a display element, a light source for electrophotography, a recording light source, an exposure light source, a reading light source, a label, a signboard, an interior design and an optical-transmission device). They can be applied to other wide range of application fields such as: organic semiconductor laser materials (a recording light source, an exposure light source, and a reading light source for light communication device and a light source for electrophotography); photoreceptor materials for electrophotography; organic TFT element materials (an organic memory device, an organic arithmetic element, an organic switching element); organic wavelength conversion element materials; and photoelectric conversion element materials (a solar cell and an optical sensor).

<Constituting Layers>

The layers which constitute the organic EL element of the present invention will now be detailed. Preferred embodiments of the organic EL element of the present invention will be described below, however, the present invention is not limited to these.

(i) anode/light emitting layer/electron transport layer/cathode
(ii) anode/hole transport layer/light emitting layer/electron transport layer/cathode
(iii) anode/hole transport layer/light emitting layer/hole blocking layer/electron transport layer/cathode
(iv) anode/hole transport layer/light emitting layer/hole blocking layer/electron transport layer/cathode buffer layer/cathode
(v) anode/anode buffer layer/hole transport layer/light emitting layer/hole blocking layer/electron transport layer/cathode buffer layer/cathode Further, it is preferable that the hole transport layer is located adjacent to the anode, and that the electron transport layer is located adjacent to the cathode.

<Pair of Electrodes>

The aforesaid a pair of electrodes is composed of an anode and a cathode, and the constituting layers including the phosphorescence emitting layer is included therebetween.

<Anode>

As an anode according to an organic EL element of the present invention, those comprising a metal, an alloy, a conductive compound, which is provided with a large work function (not less than 4 eV), and a mixture thereof as an electrode substance are preferably utilized. Specific examples of such an electrode substance include a conductive transparent material such as metal like Au, CuI, indium tin oxide (ITO), SnO₂ and ZnO. Further, a material such as IDIXO (In₂O₃—ZnO), which can produce an amorphous and transparent electrode, may be also utilized.

As for an anode, these electrode substances may be made into a thin layer by a method such as evaporation or spattering and a pattern of a desired form may be knitted by means of photolithography, or in the case of requirement of pattern precision is not so severe (not less than 100 μm), a pattern may be formed through a mask of a desired form at the time of evaporation or spattering of the above-described substance. Alternatively, when coatable materials such as organic electrically conductive compounds are employed, it is possible to employ a wet system filming method such as a printing system or a coating system. When emission is taken out of this anode, the transmittance is preferably set to not less than 10% and the sheet resistance as an anode is preferably not more than a few hundreds Ω/□. Further, although the layer thickness depends on a material, it is generally selected in a range of 10-1,000 nm and preferably of 10-200 nm.

<Cathode>

On the other hand, as a cathode according to the present invention, a metal which have a small work function (not more than 4 eV, it is called as an electron injecting metal), an alloy, a conductive compound and a mixture thereof, are utilized as an electrode substance. Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture and rare earth metal.

Among them, with respect to an electron injection property and durability against such as oxidation, preferable are: a mixture of electron injecting metal with a second metal which is stable metal having a work function larger than electron injecting metal. Examples are: a magnesium/silver mixture, a magnesium/aluminum mixture, a magnesium/indium mixture, an potassium/aluminum mixture and aluminum. As for a cathode, these electrode substances may be made into a thin layer by a method such as evaporation or spattering.

Further, the sheet resistance as a cathode is preferably not more than a few hundreds Ω/□ and the layer thickness is generally selected in a range of 10 nm-5 µm and preferably of 50-200 nm. Herein, to transmit emission, either one of an anode or a cathode of an organic EL element is preferably transparent or translucent to improve the emission luminance.

Further, after forming, the above metals at a film thickness of 1 nm-20 nm on the cathode, it is possible to prepare a transparent or translucent cathode in such a manner that electrically conductive transparent materials are prepared thereon. By applying the above, it is possible to produce an element in which both anode and cathode are transparent.

Next, the injection layer, the blocking layer and the electron transport layer, which are used as the constituting layers of the organic EL element of the present invention will be described.

<Injection Layer: Electron Injection Layer, Hole Injection Layer>

An injection layer is appropriately provided and includes an electron injection layer and a hole injection layer, which may be arranged between an anode and an emitting layer or a positive transfer layer, and between a cathode and an emitting layer or an electron transport layer, as described above.

An injection layer is a layer which is arranged between an electrode and an organic layer to decrease an operating voltage and to improve an emission luminance, which is detailed in volume 2, chapter 2 (pp. 123-166) of "Organic EL Elements and Industrialization Front thereof (Nov. 30, 1998, published by N. T. S Corp.)", and includes a hole injection layer (an anode buffer layer) and an electron injection layer (a cathode buffer layer).

An anode buffer layer (a hole injection layer) is also detailed in such as JP-A Nos. 9-45479, 9-260062 and 8-288069, and specific examples include such as a phthalocyanine buffer layer comprising such as copper phthalocyanine, an oxide buffer layer comprising such as vanadium oxide, an amorphous carbon buffer layer, and a polymer buffer layer employing conductive polymer such as polyaniline (or called as emeraldine) or polythiophene.

A cathode buffer layer (an electron injection layer) is detailed in JP-A Nos. 6-32587, 9-17574 and 1074586. Specific examples include: a metal buffer layer made of such as strontium and aluminum; an oxide buffer layer made of such as aluminum oxide; a metal or metal compound buffer layer made of such as lithium fluoride; alkali earth metal compound buffer layer made of magnesium fluoride. The above-described buffer layer (injection layer) is preferably a very thin layer, and the layer thickness is preferably in a range of 0.1 nm-5 µm although it depends on a raw material.

<Blocking Layer: Hole Blocking Layer, Electron Blocking Layer>

An blocking layer is appropriately provided in addition to the basic constitution layers composed of organic thin layers as described above. Examples are described in such as JP-A Nos. 11-204258 and 11-204359 and p. 273 of "Organic EL Elements and Industrialization Front Thereof (Nov. 30, 1998), published by N. T. S Corp.)" is applicable to a hole blocking (hole block) layer according to the present invention.

A hole blocking layer, in abroad meaning, is provided with a function of electron transport layer, being composed of a material having a function of transporting an electron but a very small ability of transporting a hole, and can improve the recombination probability of an electron and a hole by blocking a hole while transporting an electron.

The hole blocking layer of the organic EL element of the present invention is arranged adjacent to the light emitting layer.

In the present invention, it is preferable to incorporate the compound relating to the present invention as described as a hole blocking material in a hole blocking layer. By this, it can be produced an organic EL element exhibiting higher light emitting efficiency with longer lifetime.

On the other hand, the electron blocking layer, as described herein, has a function of the hole transport layer in a broad sense, and is composed of materials having markedly small capability of electron transport, while having capability of transporting holes and enables to enhance the recombination probability of electrons and holes by inhibiting electrons, while transporting electrons.

<Light Emitting Layer>

The light emitting layer of the present invention is a layer, which emits light via recombination of electrons and holes injected from an electrode or a layer such as an electron transport layer or a hole transport layer. The light emission portion may be present either within the light emitting layer or at the interface between the light emitting layer and an adjacent layer thereof.

<Phosphorescence Emitting Dopants>

The aforesaid light emitting layer contains a host compound and a light emitting dopant. As light emitting dopants, it can be employed fluorescent dopants and phosphorescent dopants (also referred to as phosphorescent compounds, or phosphorescence emitting materials). It is preferable to use phosphorescent dopants. A phosphorescence emitting layer contains a phosphorescent dopant as a dopant.

(Host Compounds)

In a light emitting layer of an organic EL element of the present invention, it is preferable to contain a host compound and a phosphorescent compound listed below. In the present invention, it is preferable to use the aforesaid compound according to the present invention as a host compound. By using this, a light emitting efficiency can be further increased. In addition, it may be used other compound which is not listed in the aforesaid compound according to the present invention as a host compound.

"Host compounds", as described in the present invention, are defined as compounds exhibiting a phosphorescent quantum yield of the phosphorescence emission of less than 0.01 at room temperature (25° C.).

An host compound of the present invention may be used with plural known host compounds. It is possible to control the transfer of charges by making use of a plurality of host compounds, which results in high efficiency of an organic EL element. In addition, it is possible to mix a different emission lights by making use of a plurality of phosphorescent compounds. Any required emission color can be obtained thereby. It may be possible to achieve white light emission by controlling the kinds and dope amount of phosphorescent compounds. It can be applied to illumination and backlight.

A known light emitting host (or emission host) which may be used in the present invention is preferably a compound having a hole transporting ability and an electron transporting ability, as well as preventing elongation of an emission wavelength and having a high Tg (a glass transition temperature).

As specific examples of a host compound, the compounds described in the following Documents are preferable.

For example, JP-A Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

The light emitting layer may contain a host compound which exhibits a fluorescent maximum wavelength as a host compound. In this case, by energy transfer to the fluorescent compound from other host compound and the phosphorescent compound, electric field emission can be obtained from other host compound having a fluorescent maximum wavelength from an organic EL element. Preferable host compounds exhibiting a fluorescent maximum wavelength are compounds having high quantum efficiency in a liquid condition. The quantum efficiency is preferable to be 10% or more and especially preferable to be 30% or more.

The specific examples of a host compound exhibiting a fluorescent maximum wavelength are: coumarin based dyes, pyran based dyes, cyanine based dyes, croconium based dyes, squarylium based dyes, oxobenzanthracene based dyes, fluorescein based dyes, Rhodamine based dyes, pyrylium based dyes, perylene based dyes, stilbene based dyes and polythiophene based dyes. The fluorescence quantum yield can be determined via a method described in page 398 of Bunko II of Dai 4 Han Jikken Kagaku Koza 7 (Spectroscopy II of 4th Edition Lecture of Experimental Chemistry 7) (1992, published by Maruzen Co., Ltd.).

(Light Emitting Dopants)

The light emitting dopant of the present invention will be described.

As light emitting dopants according to the present invention, it can be employed fluorescent dopants (also referred to as fluorescent compounds) and phosphorescent dopants (also referred to as phosphorescence emitting materials, phosphorescent compounds or phosphorescence emitting compounds).

(Phosphorescence Emitting Compounds (Also Referred to as Phosphorescence Dopants))

A phosphorescence dopant of the present invention will be described.

The phosphorescent dopant of the present invention is a compound, wherein emission from an excited triplet state thereof is observed, specifically, emitting phosphorescence at room temperature (25° C.) and exhibiting a phosphorescence quantum yield of at least 0.01 at 25° C. The phosphorescence quantum yield is preferably at least 0.1.

The aforesaid phosphorescence quantum yield can be determined via a method described in page 398 of Bunko II of Dai 4 Han Jikken Kagaku Koza 7 (Spectroscopy II of 4th Edition Lecture of Experimental Chemistry 7) (1992, published by Maruzen Co., Ltd.). The phosphorescence quantum yield in a solution can be determined using appropriate solvents. However, it is only necessary for the phosphorescent dopant of the present invention to exhibit the above phosphorescence quantum yield (0.01 or more) using any of the appropriate solvents.

Two kinds of principles regarding emission of a phosphorescence emitting compound are cited. One is an energy transfer-type, wherein carriers recombine on a host compound on which the carriers are transferred to produce an excited state of the host compound, and then via transfer of this energy to a phosphorescence emitting compound, emission from the phosphorescence emitting compound is realized. The other is a carrier trap-type, wherein a phosphorescence emitting compound serves as a carrier trap and then carriers recombine on the phosphorescence emitting compound to generate emission from the phosphorescence emitting compound.

In each case, the excited state energy of the phosphorescence emitting compound is required to be lower than that of the host compound.

As phosphorescence emitting compounds relating to the preset invention, the compounds represented by Formula (5) are preferably listed,

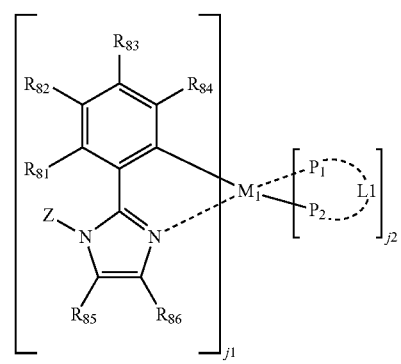

Formula (5)

In Formula, Z represents a hydrocarbon ring group, an aromatic heterocyclic group or a heterocyclic group. $R_{81}$ to $R_{86}$ each represent a hydrogen atom or a substituent. $P_1$-L1-$P_2$ represents a bidentate ligand, and $P_1$ and $P_2$ each independently represent a carbon atom, a nitrogen atom, or an oxygen atom. L1 represents a group of atoms necessary to form a bidentate ligand together with $P_1$ and $P_2$. j1 is an integer of 1 to 3, and j2 is an integer of 0 to 2, provided that the sum of j1 and j2 is 2 or 3. $M_1$ represents a transition metal element of Group 8 to Group 10 in the periodic table.

(Phosphorescence Emitting Compounds Represented by Formula (5))

The compounds represented by Formula (5) are preferably used for phosphorescence emitting compounds in the present invention.

In Formula (5), examples of a bidentate ligand represented by $P_1$-L1-$P_2$ include: substituted or unsubstituted phenylpyridine, phenylpyrazole, phenylimidazole, phenyltriazole, phenyltetrazole, pyrazabol, acetylacetone and picolinic acid.

Although $M_1$ represents a transition metal element of Group 8 to Group 10 in the periodic table (it is simply called as a transition metal), among them, iridium and platinum are preferable, and especially, platinum is preferable.

Examples of a hydrocarbon ring group represented by Z include: a non-aromatic hydrocarbon ring group and an aromatic hydrocarbon ring group. Examples of a non-aromatic hydrocarbon ring group include: a cyclopropyl group, a cyclopentyl group and a cyclohexyl group, these may be substituted or unsubstituted. Examples of an aromatic hydrocarbon ring group include: a phenyl group, a p-chlorophenyl group, a mesityl group, a tolyl group, a xylyl group, a naphthyl group, an anthryl group, an azulenyl group, an acenaphthenyl group, a fluorenyl group, a phenantolyl group, an indenyl group, a pyrenyl group, and a biphenyryl group. These may be substituted or unsubstituted.

In Formula (5), $R_{81}$ to $R_{86}$ each represents a hydrogen atom or a substituent. Examples of a substituent include: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); a cycloalkyl group (for example, a cyclopentyl group, and a cyclohexyl group); an alkenyl group (for example, a vinyl group and an allyl group); an alkynyl group (for example, an ethynyl group and a propargyl group); an aromatic hydrocarbon ring group (also called an aromatic carbon ring or an aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenantolyl group, an indenyl group, a pyrenyl group, and a biphenyryl group); an aromatic heterocyclic group (for example, a pyridyl group, a pyrimidinyl group, a furyl group, a pyrrolyl group, an imidazolyl group, a benzoimidazolyl group, a pyrazolyl group, a pyradinyl group, a triazolyl group (for example, 1,2,4-triazole-1-yl group and 1,2,3-triazole-1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, a carbolinyl group, a diazacarbazolyl group (indicating a ring structure in which one of the carbon atoms constituting the carboline ring in the aforesaid carbolinyl group is replaced with a nitrogen atom), a quinoxalinyl group, a pyridazinyl group, a triazinyl group, a quinazolinyl group, and a phthalazinyl group), a quinoxalinyl group, a pyridazinyl group, a triazinyl group, a quinazolinyl group, a phthalazinyl group); a heterocyclic group (for example, a pyrrolidyl group, an imidazolidyl group, a morpholyl group, and an oxazolidyl group); an alkoxyl group (for example, a methoxy group, an ethoxy group, a propyloxy group, a pentyloxy group, an hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, a hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-oyridylaminoureido group); a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group, an arylsulfonyl group or a heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a dodecylamino group, an anilino group, a naphthylamino group, and a 2-pyridylamino group); a cyano group; a nitro group; a hydroxyl group; a mercapto group; a silyl group (for example, a trimethylsilyl group, a triisopropylsilyl group, a triphenylsilyl group, and a phenyldiethylsilyl group) and a phosphono group.

Moreover, these substituents may be further substituted by the above-mentioned substituent. Further, a plurality of these substituents may combine with each other to form a ring.

Specific compounds represented by Formula (5) are listed below, however, the present invention is not limited to them. These compounds can be synthesized by the method described in, for example, Inorganic Chemistry vol. 40, No. 7, pp. 1704-1711.

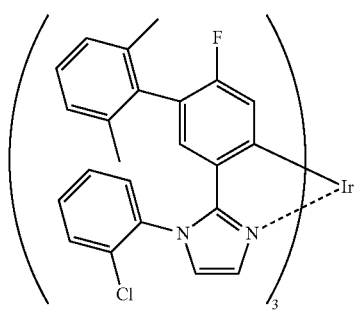
D-001
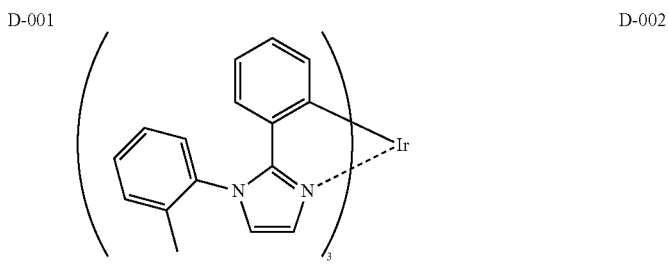
D-002
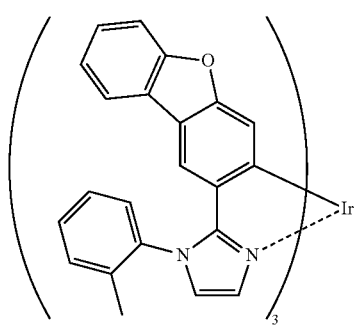
D-003
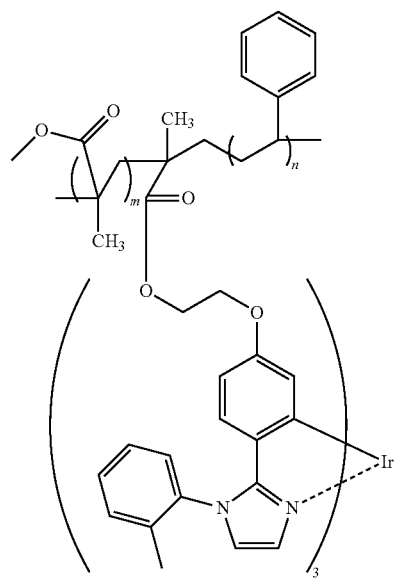
D-004
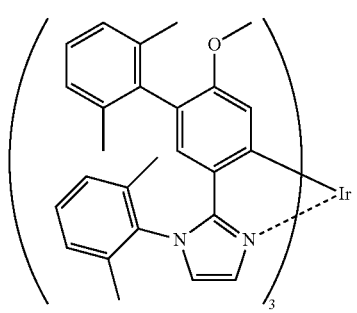
D-005
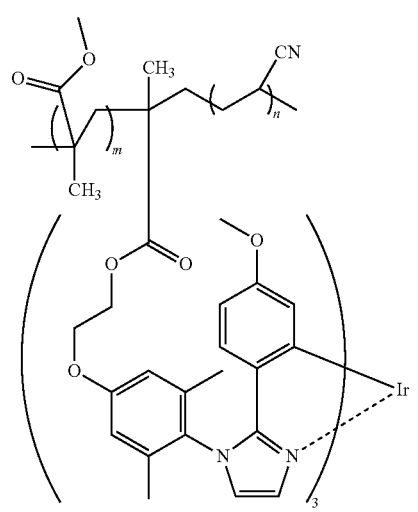
D-006

-continued
D-007
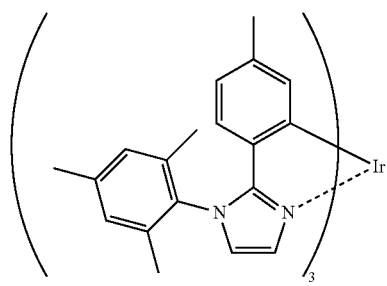
D-008
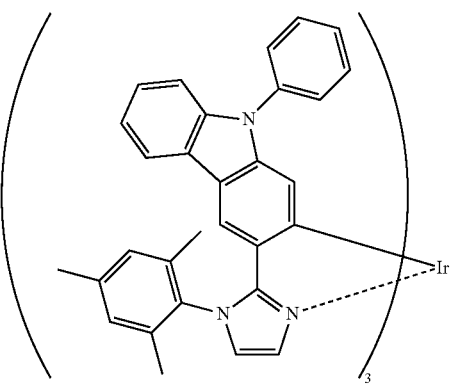
D-009
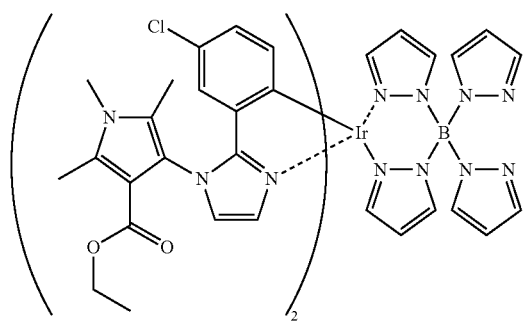
D-010
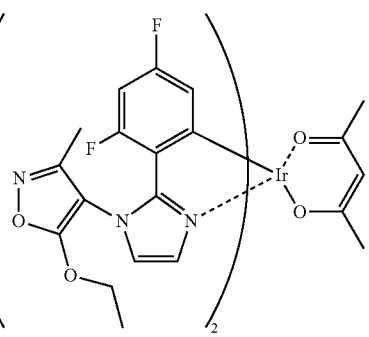
D-011
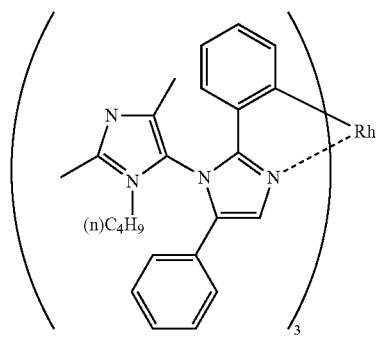
D-012
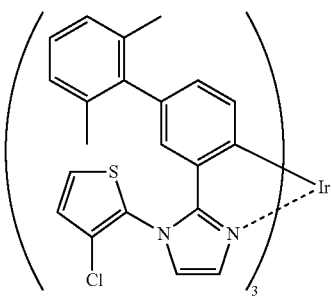
D-013
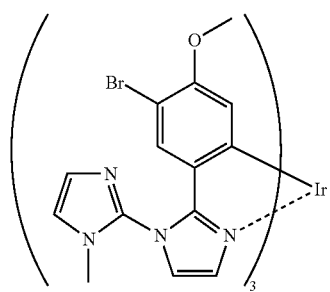
D-014
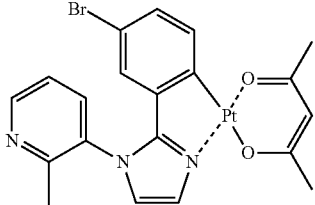
D-015
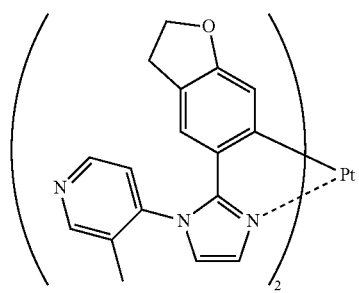
D-016
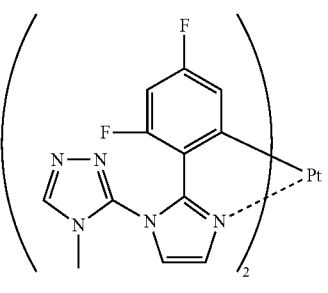

-continued
D-017
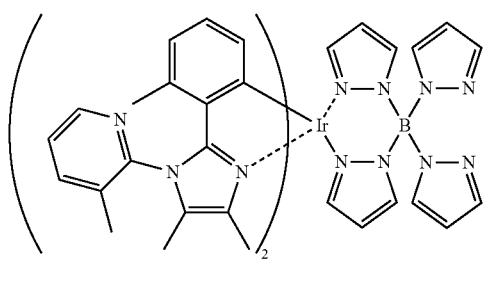
D-018
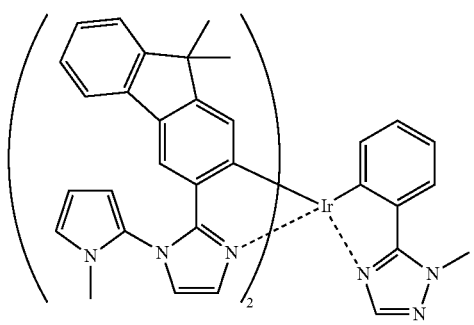
D-019
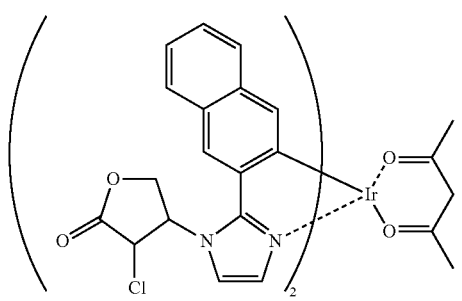
D-020
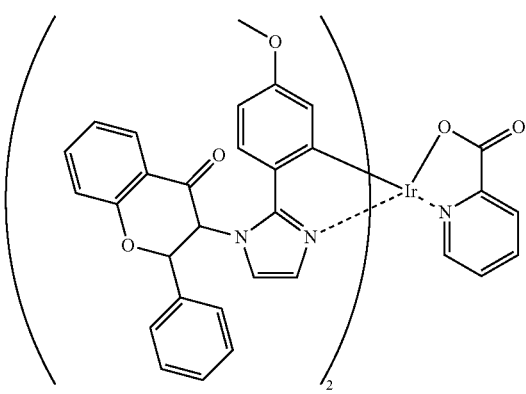
D-021
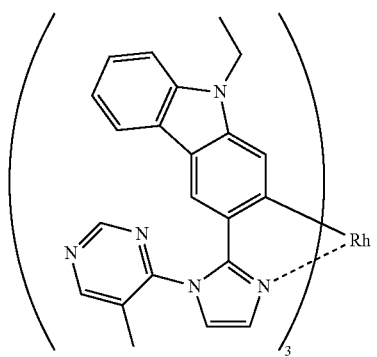
D-022
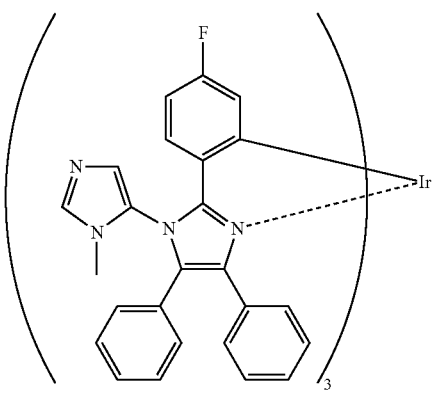
D-023
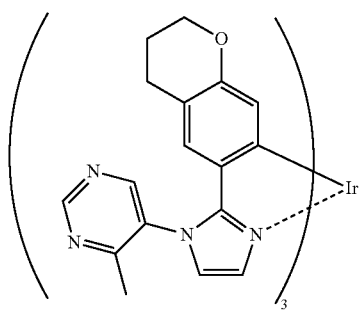
D-024
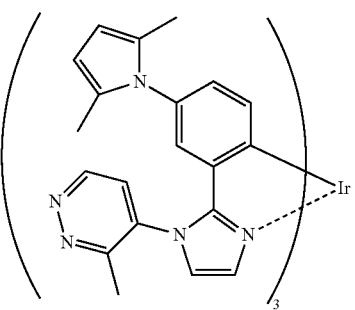

-continued
D-025
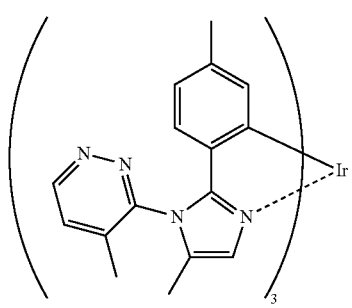
D-026
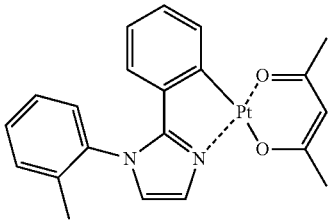
D-027
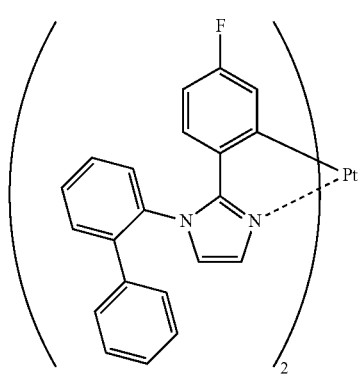
D-028
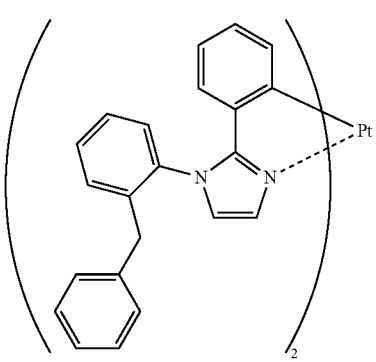
D-029
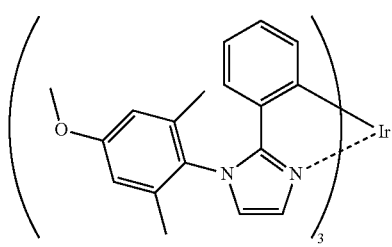
D-030
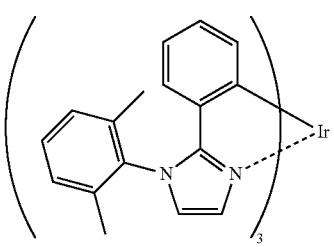
D-031
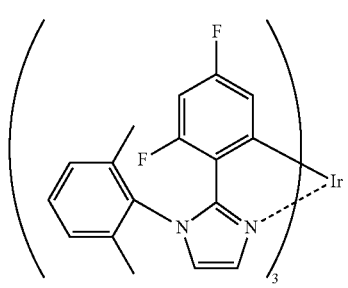
D-032
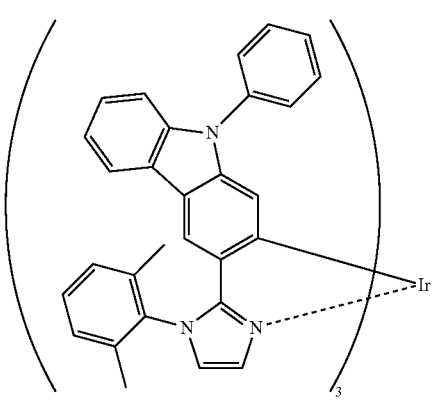
D-033
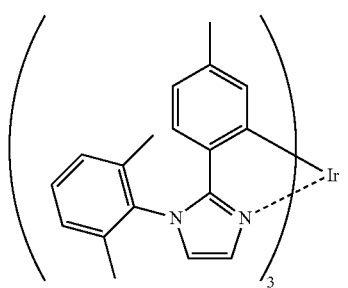
D-034
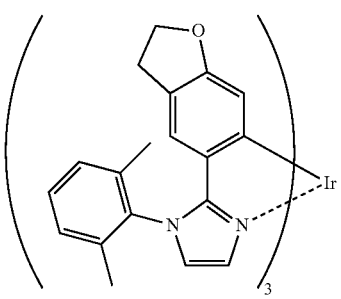

-continued
| D-035 | D-036 |
|---|---|
| 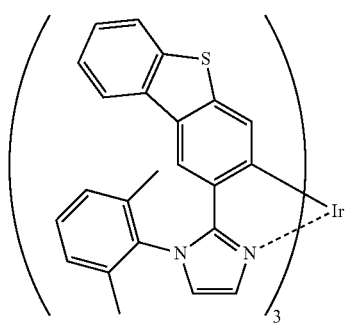 | 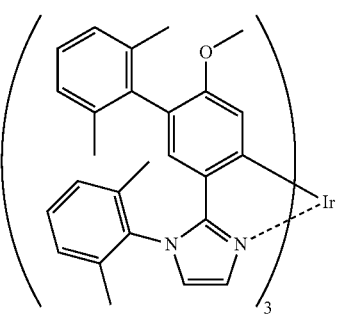 |
| D-037 | D-038 |
|---|---|
| 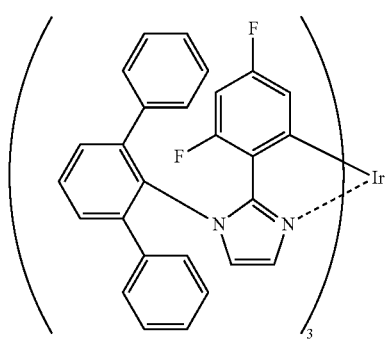 | 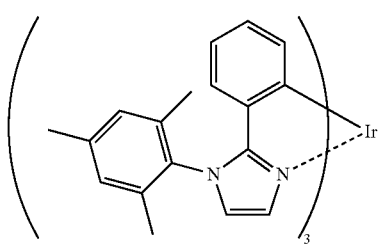 |
| D-039 | D-040 |
|---|---|
| 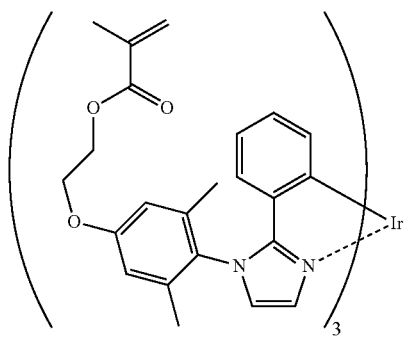 | 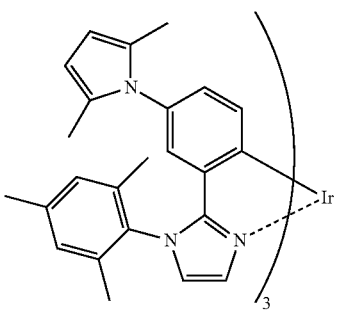 |
| D-041 | D-042 |
|---|---|
| 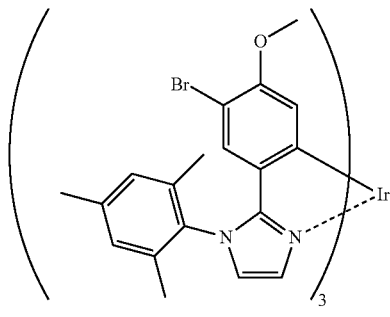 | 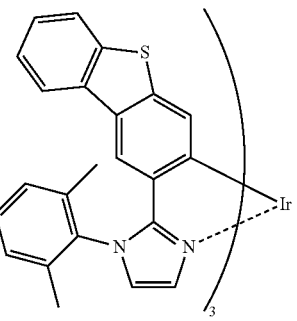 |
| D-043 | D-044 |
|---|---|
| 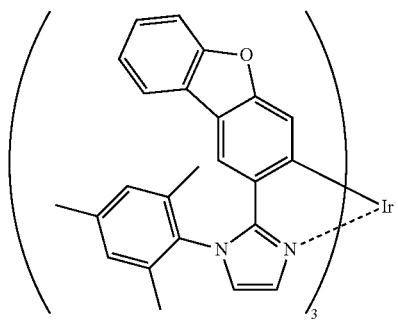 | 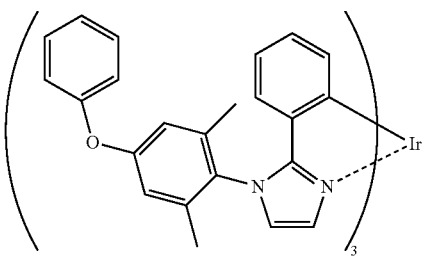 |

D-045
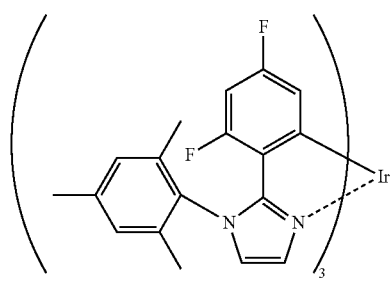
D-046
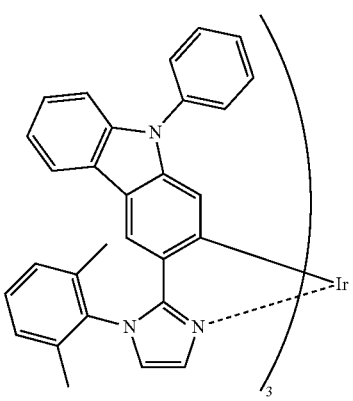
D-047
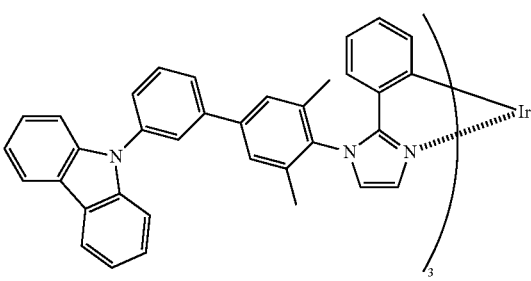
D-048
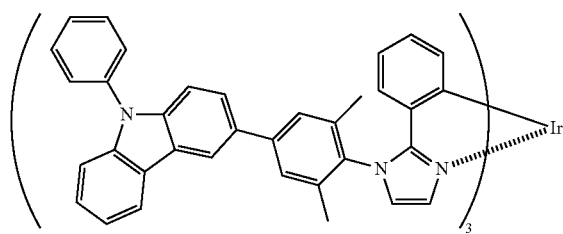
D-049
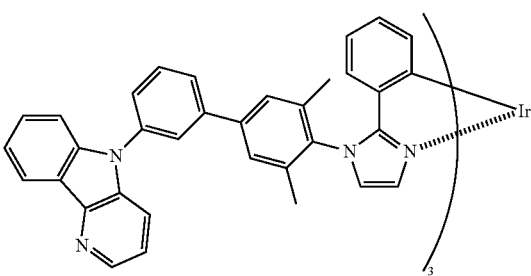
D-050
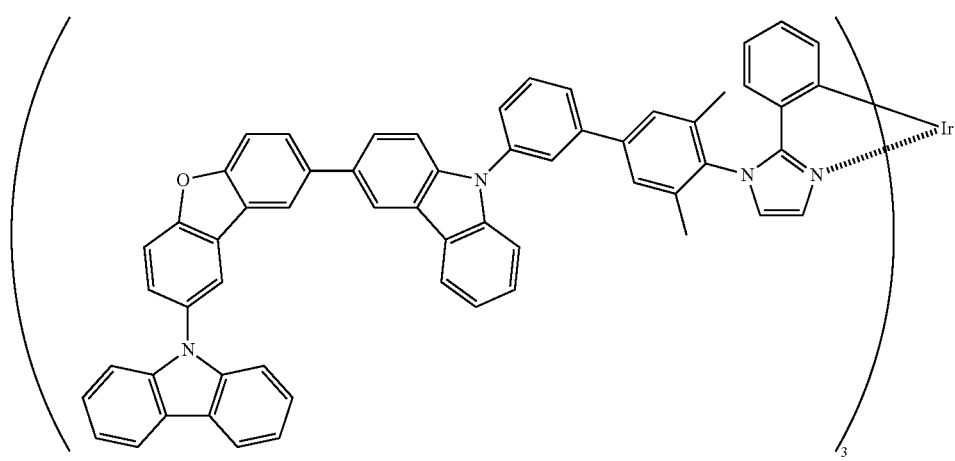
D-051

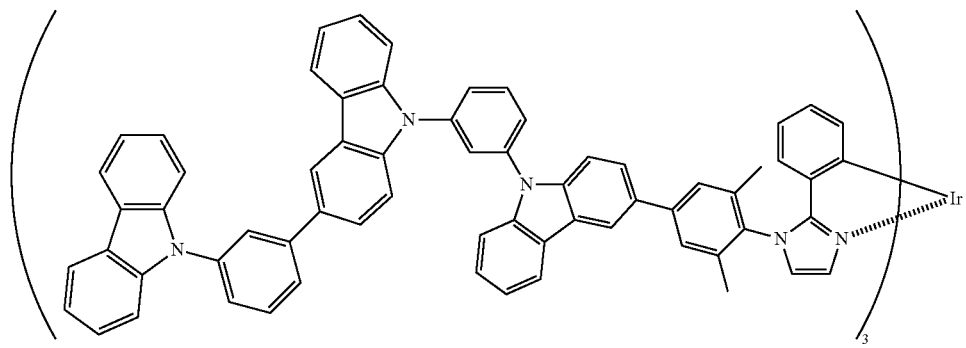

D-052

An organic EL element of the present invention may contain other phosphorescence emitting compound suitable selected from the known compounds in combination with the compound represented by Formula (5). Specific examples of the phosphorescence emitting compound which may be used in combination with the compound represented by Formula (5) are listed below.

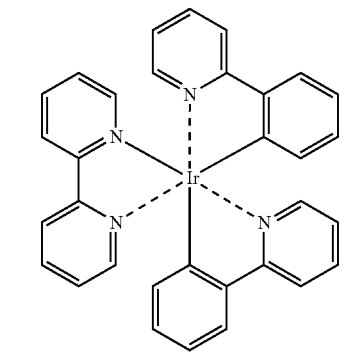

Ir-1

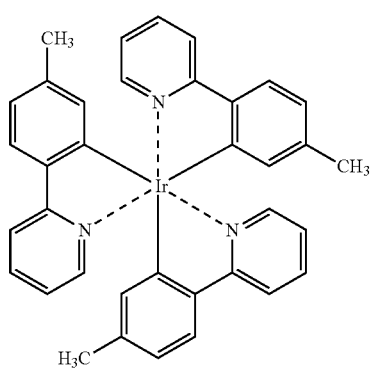

Ir-2

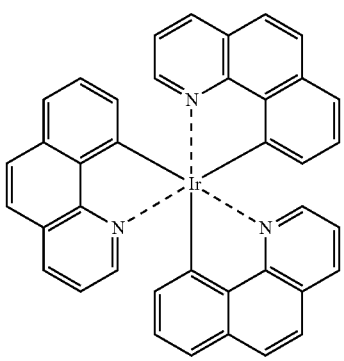

Ir-3

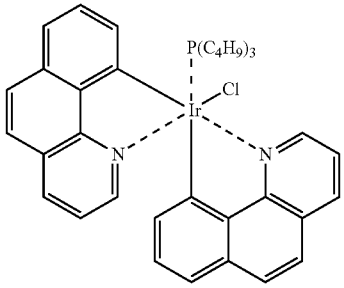

Ir-4

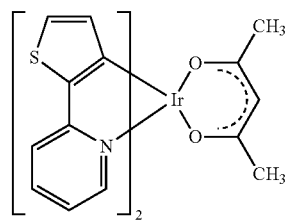

Ir-5

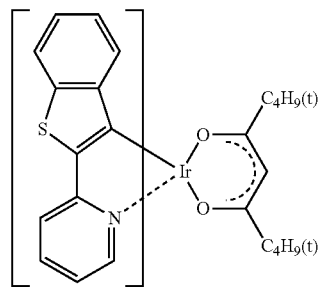

Ir-6

Ir-7
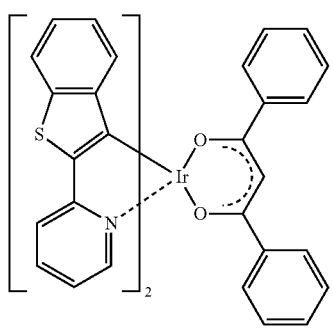
Ir-8
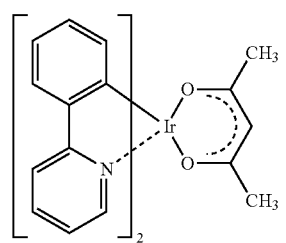
Ir-9
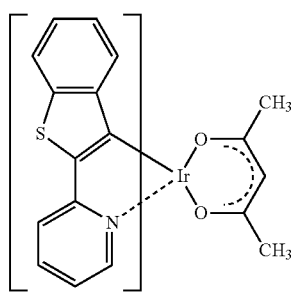
Ir-10
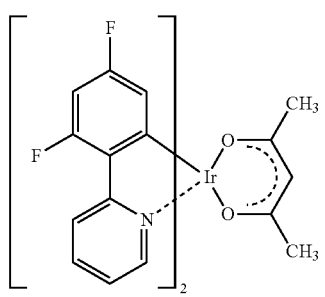
Ir-11
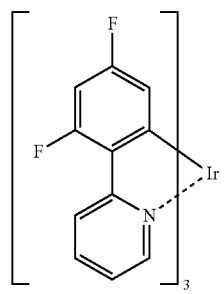
Ir-12
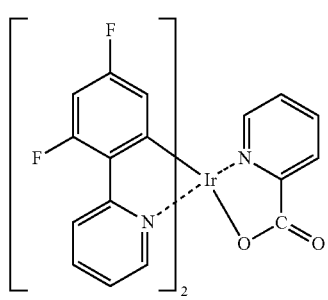
Ir-13
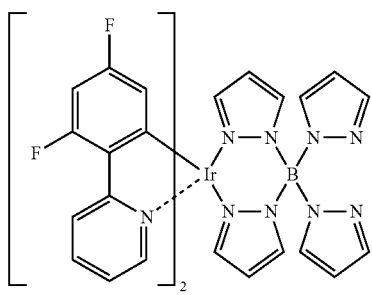
Ir-14
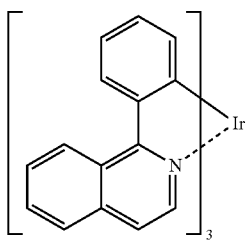
Ir-15
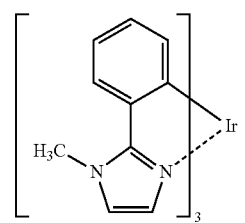
Pt-1
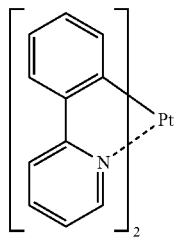
Pt-2

-continued
Pt-3
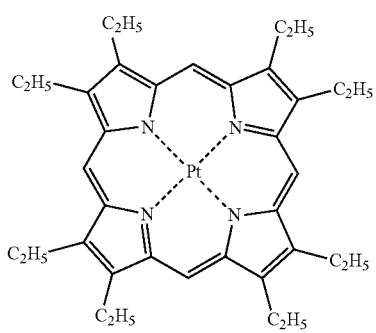
A-1
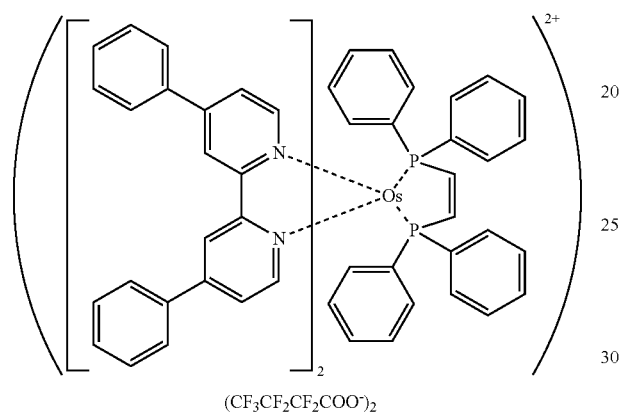
$(CF_3CF_2CF_2COO^-)_2$
D-1
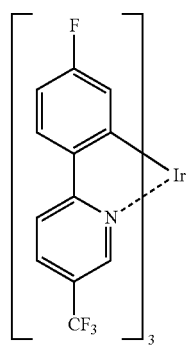
-continued
D-4
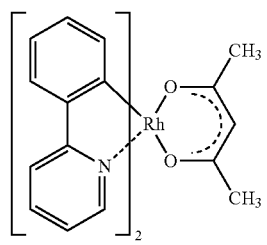
D-5
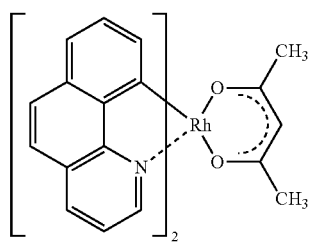
D-6
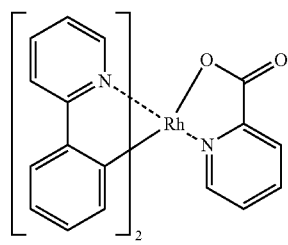
Pd-1
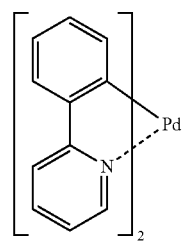
Pd-2
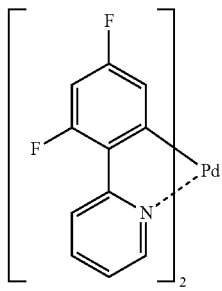
Pd-3
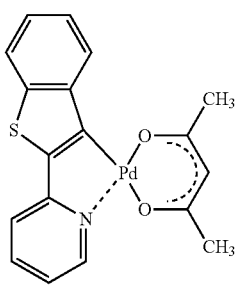

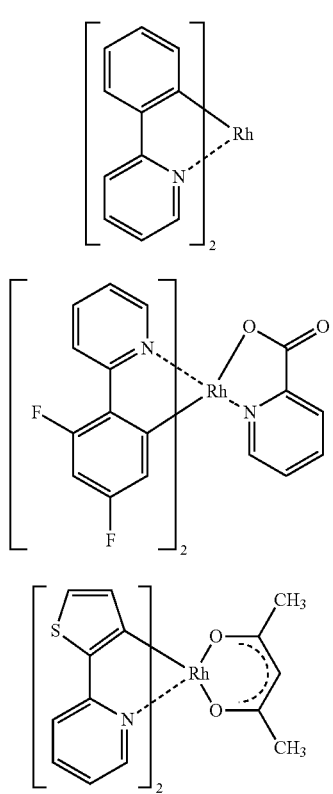

(Fluorescent Dopants (Also Referred to as Fluorescent Compounds))

As fluorescent dopants, listed are compounds exhibiting a high fluorescent quantum efficiency such as: coumarin based dyes, pyran based dyes, cyanine based dyes, croconium based dyes, squarylium based dyes, oxobenzanthracene based dyes, fluorescein based dyes, Rhodamine based dyes, pyrylium based dyes, perylene based dyes, stilbene based dyes, polythiophene based dyes, rare earth complex based fluorescent materials, or laser dyes. These compounds may be used in combination with the compound represented by Formula (5).

The light emitting layer can be prepared by forming a thin layer made of the above-described compounds according to a method well known in the art such as a vacuum evaporation method, a spin coating method, a cast method, and an inkjet method. The layer thickness of the light emitting layer is not specifically limited, however, it is generally 5 nm to 5 μm, and preferably 5 nm to 200 nm. This light emitting layer may be a single layer structure composed of one or plural types of the phosphorescent compounds and the host compounds, or it may be a laminated structure composed of a plurality of layers each containing the same or different composition.

<Hole Transport Layer>

A hole transport layer contains a material having a function of transporting a hole, and in a broad meaning, a hole injection layer and an electron blocking layer are also included in a hole transport layer. A single layer of or plural layers of a hole transport layer may be provided.

A hole transport material is those having any one of a property to inject or transport a hole or a bather property to an electron, and may be either an organic substance or an inorganic substance. Examples thereof are: a triazole derivative, an oxadiazole derivative, an imidazole derivative, a polyarylalkane derivative, a pyrazolone derivative, a phenylenediamine derivative, an arylamine derivative, an amino substituted chalcone derivative, an oxazole derivatives, a styrylanthracene derivative, a fluorenone derivative, a hydrazone derivative, a stilbene derivative, a silazane derivative, an aniline type copolymer, or conductive polymer oligomer and specifically preferably such as thiophene oligomer.

As a hole transport material, those described above can be utilized, however, it is preferable to utilized a porphyrin compound, an aromatic tertiary amine compound and a styrylamine compound, and specifically preferably an aromatic tertiary amine compound.

Typical examples of an aromatic tertiary amine compound and a styrylamine compound include: N,N,N',N'-tetraphenyl-4,4'-diaminophenyl; N,N'-diphenyl-N,N'-bis(3-methylphenyl)-(1,1'-biphenyl)-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl 4,4'-diaminobiphenyl; 1,1-bis(4-di-p-tolylaminophenyl)-4-phenylcyclohexane; bis(4-dimethylamino-2-methyl) phenylmethane; bis(4-di-p-tolylaminophenyl) phenylmethane; N,N'-diphenyl-N,N'-di(4-methoxyphenyl)-4,4'-diaminobiphenyl; N,N,N',N'-tetraphenyl-4,4'-diaminophenylether; 4,4'-bis(diphenylamino)quadriphenyl; N,N,N-tri(p-tolyl)amine; 4-(di-p-tolylamino)-4'-[4-(di-p-triamino)styryl]stilbene; 4-N,N-diphenylamino-(2-diphenylvinyl)benzene; 3-methoxy-4'-N,N-diphenylaminostilbene; and N-phenylcarbazole, in addition to those having two condensed aromatic rings in a molecule described in U.S. Pat. No. 5,061,569, such as 4,4'-bis[N-(1-naphthyl)-N-phenylamino]biphenyl (NDP), and 4,4',4"-tris[N-(3-methylphenyl)-N-phenylamino]triphenylamine (MDTDATA), in which three of triphenylamine units are bonded in a star burst form, described in JP-A No. 4308688.

Polymer materials, in which these materials are introduced in a polymer chain or constitute the main chain of polymer, can be also utilized. Further, an inorganic compound such as a p type-Si and a p type-SiC can be utilized as a hole injection material and a hole transport material This hole transport layer can be prepared by forming a thin layer made of the above-described hole transport material according to a method well known in the art such as a vacuum evaporation method, a spin coating method, a cast method, an inkjet method and a LB method. The layer thickness of a hole transport layer is not specifically limited, however, it is generally 5 nm to 5 μm, and preferably 5 nm to 200 nm. This positive transport layer may have a single layer structure composed of one or not less than two types of the above described materials.

<Electron Transport Layer>

An electron transport layer is composed of a material having a function to transfer an electron, and an electron injection layer and a hole blocking layer are included in an electron transport layer in a broad meaning. A single layer or plural layers of an electron transport layer may be provided.

In the past, when a mono or plural electron transport layers are arranged in the position nearer to the cathode with respect to an emission layer, the only requirement for an electron transport material (it is used as a hole blocking material) used thereof is to have a function to transmit an electron injected from a cathode to an emission layer. The compounds conventionally well known in the art can be utilized by arbitral selection as a material thereof. Examples of a material utilized in this electron transport layer include such as a nitro-substituted fluorene derivative, a diphenylquinone derivative, a thiopyradineoxide derivative, carbodiimide, a fluorenylidenemethane derivative, anthraquinonedimethane, an anthrone derivative, and an oxadiazole derivative.

Further, a thiazole derivative in which an oxygen atom in the oxadiazole ring of the above-described oxadiazole derivative is substituted by a sulfur atom, and a quinoxaline derivative having a quinoxaline ring which is known as an electron attracting group can be utilized as an electron transport material. Polymer materials, in which these materials are introduced in a polymer chain or these materials form the main chain of polymer, can be also utilized.

Further, a metal complex of a 8-quinolinol derivative such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, can be also utilized as an electron transfer material.

Further, metal-free or metal phthalocyanine, or those the terminal of which is substituted by an alkyl group and a sulfonic acid group, can be preferably utilized as an electron transport material. Further, distyrylpyrazine derivative, which has been exemplified as a material of a light emitting layer, can be also utilized as an electron transport material, and, similarly to the case of a hole injection layer and a hole transport layer, an inorganic semiconductor such as an n-type-Si and an n-type-SiC can be also utilized as an electron transport material.

This electron transport layer can be prepared by forming a thin layer made of the above-described electron transport material according to a method well known in the art such as a vacuum evaporation method, a spin coating method, a cast method, an inkjet method and a LB method. The layer thickness of an electron transport layer is not specifically limited; however, it is generally 5 nm to 5,000 μm, more preferably, it is 5 to 200 nm. The electron transport layer may have a single layer structure composed of one or plural types of the above described materials.

<Substrate>

An organic EL element of the present invention is preferably formed on a substrate.

A substrate (it is also called as a support plate, a support material, or a support) according to an organic EL element of the present invention is not specifically limited with respect to types of such as glass and plastics. As long as they are transparent, they are not specifically limited. Substrates preferably utilized includes such as glass, quartz and transparent resin film. A specifically preferable substrate is resin film capable of providing an organic EL element with a flexible property.

Examples of a resin film includes films such as: polyethylene terephthalate (PET), polyethylene naphthalate (PEN); polyether sulfone (FES), polyether imide, polyether ether ketone, polyphenylene sulfide, polyarylate, polyimide, polycarbonate (PC), cellulose triacetate (TAC), and cellulose acetate propionate (CAP). On the surface of a resin film, it may be formed a film incorporating an inorganic or an organic compound or a hybrid film incorporating both compounds.

The external extraction efficiency of light emitted by the organic EL element of the present invention is preferably at least 1% at room temperature, but is more preferably at least 5%. External quantum yield (%)=(the number of photons emitted by the organic EL element to the exterior/the number of electrons fed to organic EL element)×100

Further, even by simultaneously employing color hue improving filters such as a color filter, simultaneously employed may be color conversion filters which convert emitted light color from the organic EL element to multicolor by employing fluorescent materials. When the color conversion filters are employed, it is preferable that λmax of light emitted by the organic EL element is at least 480 nm.

<Preparation Method of Organic EL Element>

As one example of the preparation method of the organic EL element of the present invention, there will be described the preparation method of the organic EL element composed of: anode/hole injection layer/hole transport layer/light emitting layer/electron transport layer/electron injection layer/cathode.

Initially, a thin film composed of desired electrode substances, for example, anode substances is formed on an appropriate base material to reach a thickness of at most 1 μm, but preferably 10 to 200 nm, using a method such as an evaporation method or a sputtering method, whereby an anode is prepared. Subsequently, on the above, there are formed organic compound thin layers including a hole injection layer, a hole transport layer, a light emitting layer, an electron transport layer, an electron injection layer, a hole blocking layer, which are materials for an organic EL element.

As methods for forming a thin film of this organic compound film, although there are an evaporation method and a wet method (a spin coat method, a cast method, an inkjet method and a printing method) as described above, it is especially preferable to use an evaporation method, a spin coat method, an inkjet method and a printing method from the viewpoints of obtaining a uniform film and hardly producing a pinhole. It may be applied different film forming methods for every layer. When a evaporation method is used for film production, the condition of the evaporation changes with types of compounds to be used. Generally it is preferable to suitably select the conditions as: boat heating temperature at 50 to 450° C.; degree of vacuum of $10^{-6}$ to $10^{-2}$ Pa; evaporation rate of 0.01 to 50 nm/second; substrate temperature at −50 to 300° C.; and film thickness of 0.1 nm to 5 μm, preferably 5 to 200 nm.

After forming these layers, a desired organic EL device is obtained by preparing cathode thereon by forming a film made of a cathode material with a thickness of 1 μm or less, more preferably, with a thickness of 50 to 200 nm with an evaporation method or a sputtering method, for example. Although it is desirable to produce this organic EL element with one time vacuum formation from producing a positive hole injection layer to a cathode, it may apply a different film forming method by taking out on the way to complete the production. In that case, consideration of working under a dry inert gas atmosphere is needed.

In the case of a multicolor display device of the present invention, a shadow mask is provided only at the time of a light emitting layer formation. Since other layers are commonly used, patterning such as a shadow mask is not required and layers can be formed all over the surface by such as an evaporation method, a cast method, a spin coat method, an inkjet method and a printing method. When patterning is performed only for producing a light emitting layer, the method is not specifically limited; however, preferable are an evaporation method, an inkjet method, a spin coating method and a printing method. When an evaporation method is used, it is preferable to perform pattering using a shadow mask.

It is possible to produce with a reversed order of cathode/electron injection layer/electron transport layer/light emitting layer/hole transport layer/hole injection layer/anode. When a direct-current voltage is applied to a multicolor display device thus produced, emission can be observed via application of a voltage of about 2V-about 40 V, setting the anode as positive polarity and the cathode as negative polarity. An alternating-current voltage may optionally be applied. Incidentally, any appropriate waveform of the applied alternating current may be employed.

The display device of the present invention may be used as a display device, a display, as well as various emission light sources. In the display device and the display, display in full color can be realized using three types of organic EL elements, each of which emits blue, red, and green light.

Examples of the display device and the display include a television set, a personal computer, a mobile device, AV equipment, a teletext broadcasting display, and an in-car information display. Specifically, it is also possible to be used as a display device to reproduce still or moving images. In cases of being used as the display device to reproduce moving images, the driving method may be either a simple matrix (a passive matrix) type or an active matrix type.

Examples of the lighting device of the present invention include household lighting, car-interior lighting, backlights for watches or liquid crystals, light sources for advertising billboards, signal systems, and optical memory media, as well as light sources for electrophotographic copiers, optical telecommunication processors, and optical sensors, without however being limited thereto.

The organic EL element of the present invention may be used as an organic EL element provided with a resonator structure. Application purposes of such an organic EL element featuring a resonator structure include light sources for optical memory media, electrophotographic copiers, optical telecommunication processors, and optical sensors, without however being limited thereto. Further, the organic EL element may be used for any appropriate cases of the above applications via laser oscillation.

<Display Device>

The organic EL element of the present invention may be used as a kind of lamp for illumination or an exposure light. It may be used for a projection device which projects images or may be used as a display device to reproduce still or moving images directly observed. In cases of being used as the display device to reproduce moving images, the driving method may be either a simple matrix (a passive matrix) mode or an active matrix mode.

Or it is possible to produce a full color display device by using three or more sorts of organic EL elements of the present invention each having a different luminescent color. Or it is also possible to use the luminescent color of one color, for example, white light, to convert into BGR using a color filter to result in a full color. Furthermore, although it is also possible to change in a full color by converting the luminescent color of an organic EL element in other color using a color conversion filter, it is desirable that λmax of the luminescence of the organic EL element is 480 nm or less in that case.

In the following, one example of a display device provided with an organic EL element of the present invention will be explained with reference to figures.

FIG. 1 is a schematic drawing to show an example of a display device constituted of an organic EL element. It is a schematic drawing of a display, which displays image information by emission of an organic EL element, such as a mobile phone.

Display 1 is constituted of display section A having plural number of pixels and control section B which performs image scanning of display section A based on image information.

Control section B, which is electrically connected to display section A, sends a scanning signal and an image data signal to plural number of pixels based on image information from the outside and pixels of each scanning line successively emit depending on the image data signal by a scanning signal to perform image scanning, whereby image information is displayed on display section A.

Figure 2:
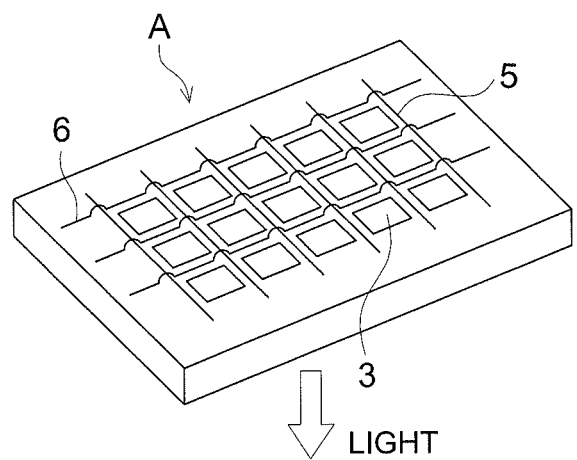
FIG. 2 is a schematic drawing of a display section A.

FIG. 2 is a schematic drawing of display section A.

Display section A is provided with such as a wiring part, which contains plural scanning lines 5 and data lines 6, and plural pixels 3 on a substrate. Primary part materials of display section A will be explained in the following. In FIG. 2, shown is the case that light emitted by pixel 3 is taken out along the white allow (downward).

Scanning lines 5 and plural data lines 6 in a wiring part each are composed of a conductive material, and scanning lines 5 and data lines 6 are perpendicular in a grid form and are connected to pixels 3 at the right-angled crossing points (details are not shown in the drawing).

Pixel 3 receives an image data from data line 6 when a scanning signal is applied from scanning line 5 and emits according to the received image data. Full color display device is possible by appropriately arranging pixels having an emission color in a red region, pixels in a green region and pixels in a blue region, side by side on the same substrate.

Next, an emission process of a pixel will be explained.

Figure 3:
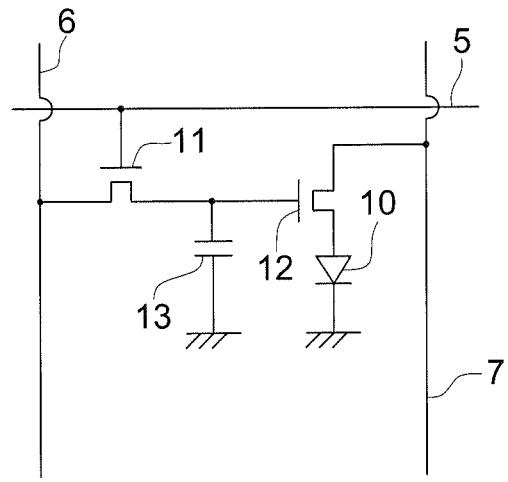
FIG. 3 is an equivalent circuit diagram of a driving circuit composing an image pixel.

FIG. 3 is a schematic drawing of a pixel.

A pixel is equipped with such as organic EL element 10, switching transistor 11, operating transistor 12 and capacitor 13. Red, green and blue emitting organic EL elements are utilized as organic EL element 10 for plural pixels, and full color display device is possible by arranging these side by side on the same substrate.

In FIG. 3, an image data signal is applied on the drain of switching transistor 11 via data line 6 from control section B. Then, when a scanning signal is applied on the gate of switching transistor 11 via scanning line 5 from control section B, operation of switching transistor is on to transmit the image data signal applied on the drain to the gates of capacitor 13 and operating transistor 12.

Operating transistor 12 is on, simultaneously with capacitor 13 being charged depending on the potential of an image data signal, by transmission of an image data signal. In operating transistor 12, the drain is connected to electric source line 7 and the source is connected to the electrode of organic EL element 10, and an electric current is supplied from electric source line 7 to organic EL element 10 depending on the potential of an image data applied on the gate.

When a scanning signal is transferred to next scanning line 5 by successive scanning of control section B, operation of switching transistor 11 is off. However, since condenser 13 keeps the charged potential of an image data signal even when operation of switching transistor 11 is off, operation of operating transistor 12 is kept on to continue emission of organic EL element 10 until the next scanning signal is applied. When the next scanning signal is applied by successive scanning, operating transistor 12 operates depending on the potential of an image data signal synchronized to the scanning signal and organic EL element 10 emits.

That is, emission of each organic EL element 10 of plural pixels 3 is performed by providing switching transistor 11 and operating transistor 12 against each organic EL element 10 of plural pixels 3. Such an emission method is called as an active matrix mode. Herein, emission of organic EL element 10 may be either emission of plural gradations based on a multiple-valued image data signal having plural number of gradation potentials or on and off of a predetermined emission quantity based on a binary image data signal.

Further, potential hold of capacitor 13 may be either continuously maintained until the next scanning signal application or discharged immediately before the next scanning signal application.

In the present invention, emission operation is not necessarily limited to the above-described active matrix mode but may be a passive matrix mode in which organic EL element is emitted based on a data signal only when a scanning signal is scanned.

Figure 4:
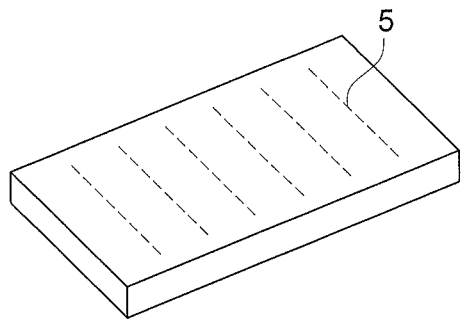
FIG. 4 is a schematic drawing of a display device according to a passive matrix mode.
Figure 4:
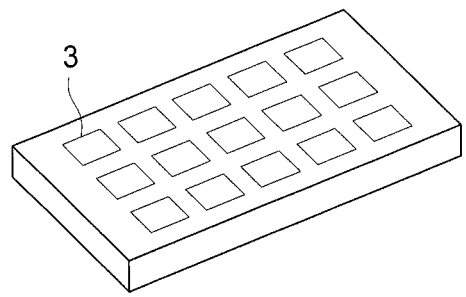
Figure 4:
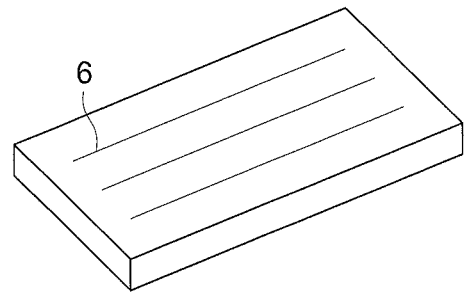

FIG. 4 is a schematic drawing of a display device based on a passive matrix mode. In FIG. 4, plural number of scanning lines 5 and plural number of image data lines 6 are arranged grid-wise, opposing to each other and sandwiching pixels 3.

When a scanning signal of scanning line 5 is applied by successive scanning, pixel 3 connected to scanning line 5 applied with said signal emits depending on an image data signal. Since pixel 3 is provided with no active element in a passive matrix mode, decrease of manufacturing cost is possible.

An organic EL element material of this invention can be also applied to an organic EL element to generate emission of practically white color as a lighting device. Plural emission colors are simultaneously emitted by plural number of emission materials to obtain white light by mixing colors. A combination of plural emission colors may be either the one, in which three emission maximum wavelengths of three primary colors of blue, green and red are contained, or the other, in which two emission maximum wavelengths, utilizing a relationship of complimentary colors such as blue and yellow, or blue and orange, are contained.

Further, a combination of emission materials to obtain plural number of emission colors may be either a combination comprising plural number of materials (emission dopants) which emit phosphoresce or fluorescence, or a combination of a material which emits phosphoresce or fluorescence and a dye material which emits by light from an emission material as exiting light, however, in a white organic electroluminescent element according to this invention, it is preferable to mix plural emission dopants in combination.

Examples of the layer constitution of an organic electroluminescent element to realize plural emission colors include a method of allowing plural emission dopants to be present in one emission region, a method of allowing one of the plural dopants exhibiting different emission wavelengths to be present in each of the emission regions, and a method of forming minute pixels, which emit light at different wavelengths, in a matrix form.

In the white organic EL element of the present invention, it is also possible to employ metal masking or patterning using ink-jet printing during layer production, as appropriate. In cases in which patterning is applied, patterning may be employed for whichever one of only an electrode, an electrode and an emission region, or the entire element layer.

An emission material utilized in a light emission layer is not specifically limited, and in the case of a backlight of a liquid crystal display element, any combination by arbitrary selection among platinum complexes according to this invention or emission materials well known in the art can be utilized so as to be fitted to the wavelength range corresponding to CF (color filter) characteristics, whereby white emission can be obtained.

In this manner, a white emitting organic EL element of this invention is usefully utilized as one type of a lamp such as a home use illumination, a car room illumination or an exposure light source as various emission light sources or lighting devices, in addition to the aforesaid display device and a display, and is further usefully applied for a display as such as a backlight of a liquid crystal display.

In addition to these, listed is a wide range of applications such as a backlight of a watch, an advertising board, a signal, a light source of an optical memory medium, a light source of an electrophotographic copier, a light source of an optical telecommunication processor and a light source of an optical sensor, and further general home use electric instruments which require a display device.

EXAMPLES

The present invention will now be described with reference to examples. However, the present invention is not limited to them.

Example 1

Preparation of Organic EL Elements 1-1 to 1-20

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

This transparent support substrate was fixed to the substrate holder of a commercial vacuum deposition apparatus. On the other hand, the following were each individually placed in a resistance heating boat made of molybdenum: 200 mg of α-NPD, 200 mg of CBP as a host compound, 200 mg of bathocuproine (BCP), 100 mg of D-038, and 200 mg of Alq$_3$. They were fitted in the vacuum deposition apparatus.

Subsequently, after reducing the pressure of the vacuum chamber to $4\times10^{-4}$ Pa, the aforesaid heating boat containing α-NPD was electrically heated to form a hole transport layer via deposition thereof onto the transparent support substrate at a deposition rate of 0.1 nm/second. Further, the two heating boats each respectively containing CBP or D-038 were electrically heated and co-deposition was carried out onto the aforesaid hole transport layer at a respective deposition rate of 0.2 nm/second and 0.012 ran/second, whereby a light emitting layer was arranged. Here, the temperature of the substrate during the deposition was room temperature.

Further, the aforesaid heating boat containing BCP was electrically heated and deposition was carried out onto the aforesaid light emitting layer at a deposition rate of 0.1 nm/second, whereby a hole blocking layer was arranged. Still further, the aforesaid heating boat containing Alq$_3$ was electrically heated and deposition was carried out onto the aforesaid hole blocking layer at a deposition rate of 0.1 nm/second, whereby an electron transport g layer having a thickness of 40 nm was arranged. Here, the temperature of the substrate during the deposition was room temperature.

Subsequently, 0.5 nm thick lithium fluoride and 110 nm thick aluminium were vapor deposited to form a cathode, whereby Organic EL element 1-1 was prepared.

Organic EL elements 1-2 to 1-20 each were prepared in the same manner as preparation of Organic EL element 1-1, except that a host compound CBP used in the light emitting layer was replaced with each of the compounds as listed in Table 1. The compounds used in the above-description are shown below.

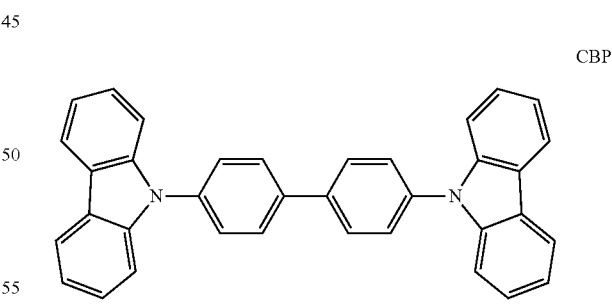

CBP

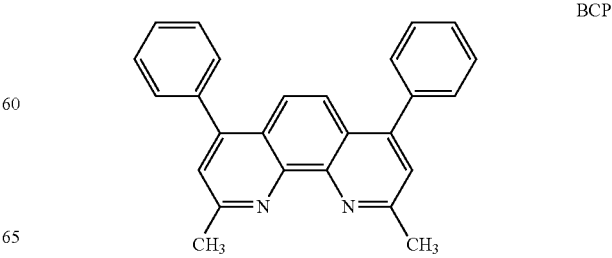

BCP

-continued

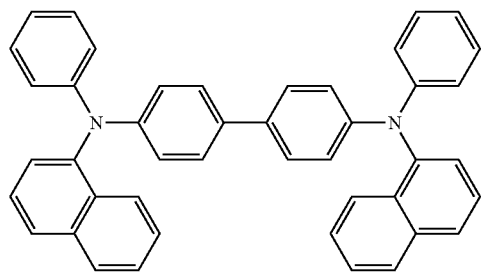
α-NPD

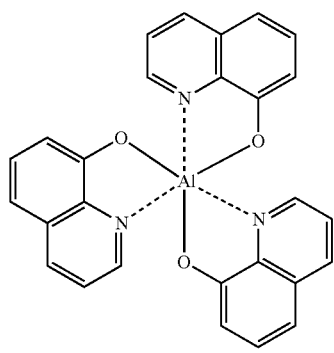
Alq₃

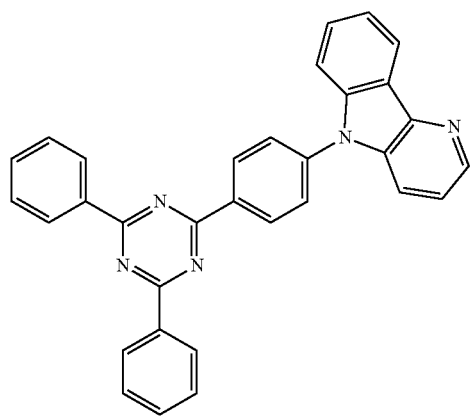
Comparative compound (1)

Evaluation of Organic EL Elements 1-1 to 1-20

The obtained Organic EL elements 1-1 to 1-20 were subjected to the following evaluations.
(Luminance)

The luminance (cd/m$^2$) was determined by using the measured luminance with Spectoradiometric luminance meter CS-1000 (produced by Konica Minolta Sensing Inc.).
(External Quantum Efficiency)

The obtained Organic EL elements were subjected to measurement of the external quantum efficiency (%) by allowing to emit a light with a constant electric current of 2.5 mA/cm$^2$ at 23° C. under a dry nitrogen gas atmosphere. Here, the measurement was done also using Spectroradiometric luminance meter CS-1000 (produced by Konica Minolta Sensing Inc.).

The measurement results of luminance and external quantum efficiency shown in the following table were represented by the relative value when the luminance and the external quantum efficiency of Organic EL element 1-1 each were set to be 100. The obtained results are shown in the following table.

TABLE 1

| Organic EL element | Host compound | Luminance | External quantum efficiency | Remarks |
|---|---|---|---|---|
| 1-1 | CBP | 100 | 100 | Comparative example |
| 1-2 | Comparative compound(1) | 89 | 79 | Comparative example |
| 1-3 | 1-2 | 170 | 160 | Inventive example |
| 1-4 | 1-4 | 178 | 165 | Inventive example |
| 1-5 | 1-5 | 173 | 172 | Inventive example |
| 1-6 | 1-7 | 180 | 180 | Inventive example |
| 1-7 | 1-10 | 188 | 190 | Inventive example |
| 1-8 | 1-11 | 190 | 189 | Inventive example |
| 1-9 | 1-15 | 180 | 186 | Inventive example |
| 1-10 | 1-17 | 180 | 186 | Inventive example |
| 1-11 | 1-21 | 177 | 175 | Inventive example |
| 1-12 | 1-23 | 187 | 185 | Inventive example |
| 1-13 | 1-25 | 185 | 186 | Inventive example |
| 1-14 | 2-1 | 193 | 192 | Inventive example |
| 1-15 | 2-3 | 195 | 194 | Inventive example |
| 1-16 | 2-10 | 196 | 197 | Inventive example |
| 1-17 | 3-1 | 199 | 199 | Inventive example |
| 1-18 | 3-3 | 202 | 202 | Inventive example |
| 1-19 | 3-4 | 201 | 201 | Inventive example |
| 1-20 | 3-8 | 200 | 201 | Inventive example |

From the results shown in the table described above, it is clear that Organic EL elements of the present invention exhibited high luminance and excellent in external quantum efficiency compared to the comparative examples.

Example 2

Preparation of Organic EL Elements 2-1 to 2-16

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

This transparent support substrate was fixed to the substrate holder of a commercial vacuum deposition apparatus. On the other hand, the following were each individually placed in a resistance heating boat made of molybdenum: 200 mg of α-NPD, 200 mg of CBP, 200 mg of BCP as a hole blocking compound, 100 mg of Ir-1, and 200 mg of Alq₃. They were fitted in the vacuum deposition apparatus.

Subsequently, after reducing the pressure of the vacuum chamber to 4×10$^4$ Pa, the aforesaid heating boat containing α-NPD was electrically heated to form a hole transport layer via deposition thereof onto the transparent support substrate at a deposition rate of 0.1 nm/second. Further, the two heating boats each respectively containing CBP or Ir-1 were electrically heated and co-deposition was carried out onto the aforesaid hole transport layer at a respective deposition rate of 0.2 nm/second and 0.012 nm/second, whereby a light emitting layer was arranged. Here, the temperature of the substrate during the deposition was room temperature.

Further, the aforesaid heating boat containing BCP was electrically heated and deposition was carried out onto the aforesaid light emitting layer at a deposition rate of 0.1 nm/second, whereby a hole blocking layer was arranged. Still further, the aforesaid heating boat containing Alq₃ was electrically heated and deposition was carried out onto the aforesaid hole blocking layer at a deposition rate of 0.1 nm/second, whereby an electron transport g layer having a thickness of 40 nm was arranged. Here, the temperature of the substrate during the deposition was room temperature.

Subsequently, 0.5 nm thick lithium fluoride and 110 nm thick aluminium were vapor deposited to form a cathode, whereby Organic EL element 2-1 was prepared.

Organic EL elements 2-2 to 2-16 each were prepared in the same manner as preparation of Organic EL element 2-1, except that BCP used as a hole blocking compound was replaced with each of the compounds as listed in the following table. The compounds used in the above-description are shown below.

Evaluation of Organic EL Elements 2-1 to 2-16

In the same manner as in Example 1, the luminance and the external quantum efficiency of Organic EL elements 2-1 to 2-16 each were evaluated. Further, the lifetime of the obtained Organic EL elements were evaluated according to the measuring method described below.

(Lifetime)

Each Organic EL element was driven with a constant electric current of 2.5 mA/cm². The time required for a decease in one half of the luminance of immediately after the initiation of light emission (being the initial luminance) was determined, and the resulting value was employed as an index of the lifetime in terms of a half lifetime (τ0.5). Here, the measurement was done with Spectroradiometric luminance meter CS-1000 (produced by Konica Minolta Sensing Inc.).

The obtained results are shown in the following table. The measurement results of luminance, external quantum efficiency and lifetime shown in the following table were represented by the relative value when the luminance, the external quantum efficiency and the lifetime of Organic EL element 2-1 each were set to be 100.

TABLE 2

| Organic EL element No. | Hole blocking compound | Luminance | External quantum efficiency | Lifetime | Remarks |
|---|---|---|---|---|---|
| 2-1 | BCP | 100 | 100 | 100 | Comparative example |
| 2-2 | 1-1 | 113 | 113 | 290 | Inventive example |
| 2-3 | 1-4 | 113 | 115 | 300 | Inventive example |
| 2-4 | 1-5 | 114 | 114 | 320 | Inventive example |
| 2-5 | 1-10 | 118 | 117 | 350 | Inventive example |
| 2-6 | 1-12 | 120 | 120 | 410 | Inventive example |
| 2-7 | 1-18 | 118 | 118 | 400 | Inventive example |
| 2-8 | 1-23 | 118 | 118 | 380 | Inventive example |
| 2-9 | 2-3 | 122 | 122 | 440 | Inventive example |
| 2-10 | 2-10 | 122 | 122 | 430 | Inventive example |
| 2-11 | 3-1 | 124 | 124 | 450 | Inventive example |
| 2-12 | 3-3 | 126 | 127 | 560 | Inventive example |
| 2-13 | 3-5 | 124 | 123 | 450 | Inventive example |
| 2-14 | 3-8 | 124 | 124 | 500 | Inventive example |
| 2-15 | 3-12 | 124 | 124 | 510 | Inventive example |
| 2-16 | 3-10 | 126 | 127 | 540 | Inventive example |

From the results shown in the table described above, it is clear that Organic EL elements of the present invention exhibited high luminance and excellent in external quantum efficiency, and achieving long lifetime compared to the comparative example.

Example 3

Preparation of Organic EL Elements 3-1 to 3-8

Organic EL elements 3-1 to 3-8 each were prepared in the same manner as preparation of Organic EL element 1-1, except that the host compound in the light emitting layer was replaced with each of the compounds as listed in the following table, D-038 was replaced with Ir-1, and BCP in the hole blocking layer was replaced with B-Alq.

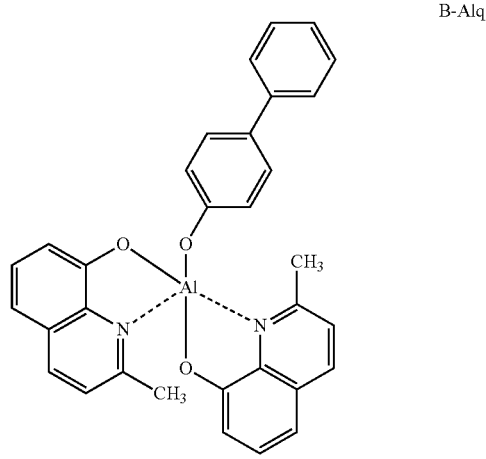

B-Alq

Evaluation of Organic EL Elements 3-1 to 3-8

Evaluation of aging stability was done according to the measuring method shown below, (Aging Stability)

Each Organic EL element was kept at aging condition of 85° C. for 24 hours. The luminance for each of Organic EL elements before aging and after aging driven at a constant current of 2.5 mA/cm² was measured. Luminance ratios of before aging and after aging were measured according to the following formula. These value were used for evaluating aging stability.

Aging stability (%)=(Luminance after kept at aging condition (2.5 mA/cm²)/Luminance before kept at aging condition (2.5 mA/cm²))×100

The obtained results are shown in the following table.

TABLE 3

| Organic EL element | Host compound | Aging stability (%) | Remarks |
|---|---|---|---|
| 3-1 | CBP | 48 | Comparative example |
| 3-2 | 1-2 | 64 | Inventive example |
| 3-3 | 1-7 | 63 | Inventive example |
| 3-4 | 1-11 | 76 | Inventive example |
| 3-5 | 1-17 | 73 | Inventive example |
| 3-6 | 2-3 | 80 | Inventive example |
| 3-7 | 2-10 | 80 | Inventive example |
| 3-8 | 3-3 | 83 | Inventive example |

From the results shown in the table described above, it is clear that Organic EL elements of the present invention are excellent in aging stability compared to the comparative example.

Example 4

Preparation of Organic EL Elements 4-1 to 4-8

Organic EL elements 4-1 to 4-8 each were prepared in the same manner as preparation of Organic EL element 2-1, except that the host compound (CEP) in the light emitting layer was replaced with Example compound 1-5, and the hole blocking compound in the hole blocking layer was replaced with the compounds as listed in the following table.

Aging stability of Organic EL elements 4-1 to 4-8 was evaluated in the same manner as described in Example 3. The obtained results are shown in the following table.

TABLE 4

| Organic EL element | Hole blocking compound | Aging stability (%) | Remarks |
|---|---|---|---|
| 4-1 | B-Alq | 67 | Comparative example |
| 4-2 | 1-3 | 73 | Inventive example |
| 4-3 | 1-10 | 77 | Inventive example |
| 4-4 | 1-12 | 79 | Inventive example |
| 4-5 | 2-2 | 80 | Inventive example |
| 4-6 | 2-10 | 82 | Inventive example |
| 4-7 | 3-3 | 84 | Inventive example |
| 4-8 | 3-10 | 83 | Inventive example |

From the results shown in the table described above, it is clear that Organic EL elements of the present invention are excellent in aging stability compared to the comparative example.

Example 5

Three organic El elements were arranged in a raw on the same substrate. The three organic El elements used were: the inventive Organic EL element 1-4 prepared in Example 1; the inventive Organic EL element 2-12 prepared in Example 2; and a red light emitting Organic EL element prepared by replacing the phosphorescent compound of Organic EL element 2-12 with Ir-9 and prepared in the same manner as preparation of Organic EL element 2-12. Thus, it was prepared a full color display device of active matrix as shown in FIG. 1. FIG. 2 shows only a schematic drawing of display section A in the prepared full color display device.

Namely, on the same substrate, the prepared full color display device has a wiring part which contains plural scanning lines 5 and data lines 6, and plural pixels 3 arranged in a raw (a pixel emitting a light of red region, a pixel of green region and a pixel of blue region). Scanning lines 5 and plural data lines 6 in a wiring part each are composed of a conductive material, and scanning lines 5 and data lines 6 are perpendicular in a grid form and are connected to pixels 3 at the right-angled crossing points (details are not shown in the drawing). The aforesaid plural pixels 3 each are Organic EL elements corresponding to each color, and driven with an active matrix mode in which a switching transistor and an operating transistor are provided. Pixel 3 receives an image data from data line 6 when a scanning signal is applied from scanning line 5 and emits according to the received image data. Thus, a full color display device is possible by appropriately arranging pixels having an emission color in a red region, pixels in a green region and pixels in a blue region, side by side on the same substrate.

By driving a full color display device, it was obtained a full color motion picture display device with a clear image.

Example 6

Preparation of Lighting Device

Figure 5:
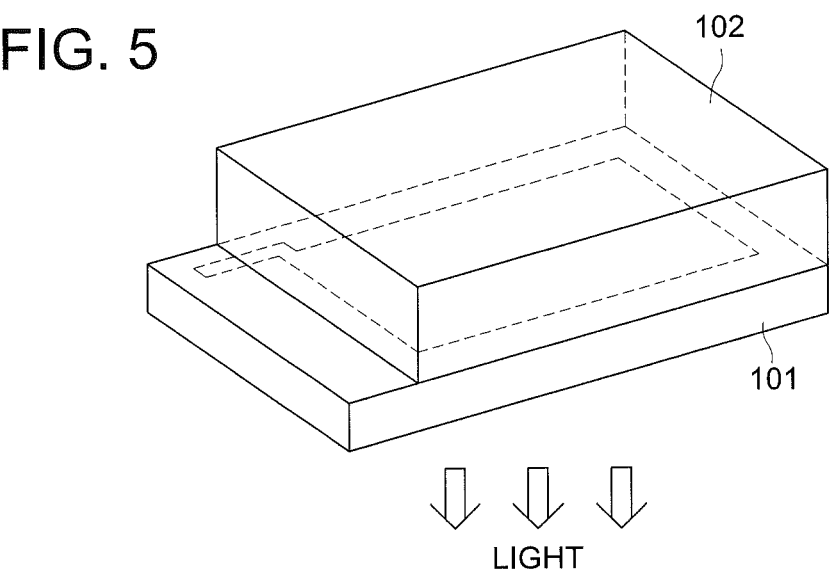
FIG. 5 is a schematic drawing of a lighting device.
Figure 6:
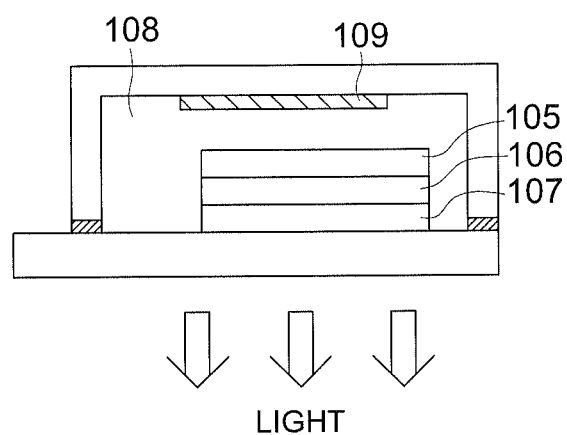
FIG. 6 is a cross-sectional drawing of a lighting device.

The non-emission sides of three organic El elements were covered with a glass case to make a lighting device. The three organic EL elements used were: Organic EL element 1-18; Organic EL element 2-12; and Organic EL element prepared by replacing the phosphorescent compound of Organic EL element 2-12 with Ir-9 and prepared in the same manner as preparation of Organic EL element 2-12. The prepared lighting device exhibited high emission efficiency and it can be used as a thin lighting device emitting a white light with a long lifetime. FIG. 5 is a schematic view of a lighting device and Organic EL element 101 is covered with glass cover 102, and FIG. 6 is a cross-sectional view of a lighting device. Numeral 105 represents a cathode, 106 represents an organic EL layer, and 107 represents a glass substrate fitted with a transparent electrode. Further, the interior of glass cover 102 is filled with nitrogen gas 108 and water catching agent 109 is provided.

Example 7

Preparation of White Light Emitting Organic EL Element 7-1

The transparent electrode support substrate prepared in Example 1 was transferred under a nitrogen atmosphere, and a solution containing 10 mg of hole injection material 1 described in WO 06/19270 dissolved in 10 ml of acetonitrile was applied thereon by using a spin coating method at 1,500 rpm for 30 seconds to form a film. The film was subjected to vacuum drying at 100° C. for 1 hour to form a hole injection layer. Further, under a nitrogen atmosphere, a solution containing hole transport material 2 dissolved in 10 ml of toluene was applied on the hole injection layer by using a spin coating method at 1,500 rpm for 30 seconds to form a film. The film was irradiated with UV rays at 150° C. for 30 seconds so as to achieve photopolymerization and cross-linking. Thus, a hole transport layer having a thickness of 20 nm was prepared.

Further, on the hole transport layer was applied a solution containing 100 mg of CBP, 10 mg of D-038 and 0.1 mg of Ir-9 dissolved in 10 ml of toluene by using a spin coating method at 1,000 rpm for 30 seconds to form a film. The film was subjected to vacuum drying at 60° C. for one hour to obtain a light emitting layer having a thickness of 50 nm.

Subsequently, on the light emitting layer was applied a solution containing 50 mg of example compound 3-3 dissolved in 10 ml of toluene by using a spin coating method at 5,000 rpm for 30 seconds to form a film. The film was subjected to vacuum drying at 60° C. for one hour to obtain an electron transport layer having a thickness of 15 nm.

Subsequently, a lithium fluoride layer and an aluminium cathode were formed as in Example 1 to obtain white light emitting Organic EL element 7-1.

The prepared Organic EL element 7-1 was applied with an electric current to obtain substantially a white light. It was proved that Organic EL element 7-1 can be used for a lighting device. In addition it was found that white light emission was achieved by replacing example compound 3-3 with other compounds relating to the present invention.

DESCRIPTION OF SYMBOLS 1 display
3 pixel
5 scanning line
6 data line
7 electrical power line
10 organic EL element
11 switching transistor
12 operating transistor
13 capacitor
A display section
B control section
102 glass cover
105 cathode
106 organic EL layer
107 glass substrate having a transparent electrode
108 nitrogen gas
109 water catching agent

The invention claimed is:

1. An organic electroluminescence element comprising a pair of electrodes and constituting layers which includes a phosphorescence emitting layer sandwiched between the pair of electrodes, wherein at least one of the constituting layers contains a compound represented by Formula (4):

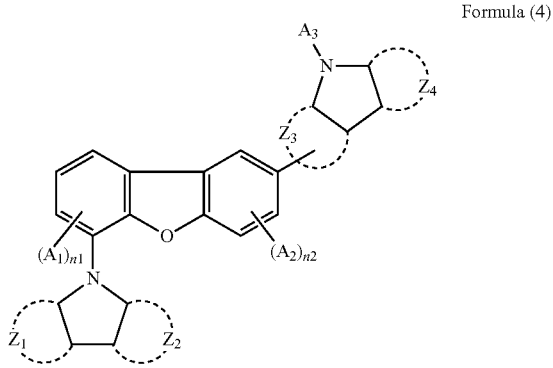

Formula (4)

wherein, $A_1$, $A_2$ and $A_3$ each represent a substituent; n1 and n2 each represent an integer of 0 to 3; and $Z_1$, $Z_2$, $Z_3$ and $Z_4$ each represent an aromatic heterocycle or an aromatic hydrocarbon ring, both of which may have a substituent, and wherein each of the $Z_1$, $Z_2$, $Z_3$, and $Z_4$ is a six membered ring containing a maximum of two nitrogen atoms and at least two of the $Z_1$, $Z_2$, $Z_3$ and $Z_4$ contain at least one nitrogen atom.

2. The organic electroluminescence element of claim 1, wherein $Z_2$ and $Z_4$ in Formula (4) each represent an aromatic heterocycle.

3. The organic electroluminescence element of claim 1, wherein the phosphorescence emitting layer contains the compound represented by Formula (4).

4. The organic electroluminescence element of claim 1, wherein the at least one of the constituting layers is a hole blocking layer and the hole blocking layer contains the compound represented by Formula (4).

5. The organic electroluminescence element of claim 1, emitting a blue light.

6. The organic electroluminescence element of claim 1, emitting a white light.

7. A display device comprising the organic electroluminescence element of claim 6.

8. A lighting device comprising the organic electroluminescence element of claim 6.

9. A display device comprising the lighting device of claim 8 and a liquid crystal element as a display means.

10. The organic electroluminescence element of claim 1, wherein $Z_1$ represents a pyridine ring, $Z_2$ represents a phenyl ring, $Z_3$ represents a phenyl ring and Z4 represents a pyridine ring.

* * * * *